(12) United States Patent
Truckai et al.

(10) Patent No.: US 7,632,269 B2
(45) Date of Patent: Dec. 15, 2009

(54) ELECTROSURGICAL INSTRUMENT WITH REPLACEABLE CARTRIDGE

(75) Inventors: Csaba Truckai, Saratoga, CA (US); John Shadduck, Tiburon, CA (US); James Baker, Palo Alto, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 661 days.

(21) Appl. No.: 11/038,930

(22) Filed: Jan. 18, 2005

(65) Prior Publication Data

US 2005/0159745 A1 Jul. 21, 2005

Related U.S. Application Data

(60) Provisional application No. 60/537,085, filed on Jan. 16, 2004.

(51) Int. Cl.
A61B 18/18 (2006.01)
(52) U.S. Cl. .......................... 606/51; 606/45
(58) Field of Classification Search ............ 606/27–32, 606/34, 37, 41, 42, 205–208, 51, 52
See application file for complete search history.

(56) References Cited

U.S. PATENT DOCUMENTS

| | | | |
|---|---|---|---|
| 659,409 A | 10/1900 | Mosher | |
| 1,586,645 A | 6/1926 | Bierman | |
| 1,798,902 A | 3/1931 | Raney | |
| 1,881,250 A | 10/1932 | Tomlinson | |
| 2,031,682 A | 2/1936 | Wappler et al. | |
| 3,651,811 A | 3/1972 | Hildebrandt et al. | |
| 3,685,518 A | 8/1972 | Beuerle et al. | |
| 3,730,188 A | 5/1973 | Ellman | |
| 3,752,161 A * | 8/1973 | Bent ........................... | 606/184 |
| 3,768,482 A | 10/1973 | Shaw | |
| 3,826,263 A | 7/1974 | Cage et al. | |
| 4,092,986 A | 6/1978 | Schneiderman | |

(Continued)

FOREIGN PATENT DOCUMENTS

EP 341 446 A2 4/1989

(Continued)

OTHER PUBLICATIONS

Burton, "New Inventions" *The Lancet*, pp. 650-651 (1959).

(Continued)

*Primary Examiner*—Michael Peffley

(57) ABSTRACT

An electrosurgical instrument with a disposable electrosurgical cartridge is provided. The cartridge has first and second energy-delivery surfaces that carry first and second opposing polarity conductors coupled to a voltage source, together with first and second temperature-responsive variable impedance bodies exposed partly in the respective-delivery surfaces. The cartridge further carries a slidable blade member. The temperature-responsive variable impedance bodies are coupled to the voltage source by series and parallel circuitry. In use, the variable impedance bodies are adapted to modulate current flow and ohmic heating in engaged tissue by providing controlled current paths in the tissue and through the variable impedance bodies as the temperature-responsive bodies sense the temperature of adjacent engaged tissue. The engagement surfaces are capable of highly localized modulation of Rf energy application to engage engaged tissue to provide high and low temperatures, voltage and current in the tissue to create high strength welds.

14 Claims, 26 Drawing Sheets

U.S. PATENT DOCUMENTS

| | | | |
|---|---|---|---|
| 4,198,957 A | 4/1980 | Cage et al. | |
| 4,219,025 A | 8/1980 | Johnson | |
| 4,231,371 A | 11/1980 | Lipp | |
| 4,232,676 A | 11/1980 | Herczog | |
| 4,271,838 A | 6/1981 | Lasner et al. | |
| 4,353,371 A | 10/1982 | Cosman | |
| 4,370,980 A | 2/1983 | Lottick | |
| 4,375,218 A | 3/1983 | Digeronimo | |
| 4,492,231 A | 1/1985 | Auth | |
| 4,590,934 A | 5/1986 | Malis et al. | |
| 4,608,981 A | 9/1986 | Rothfs et al. | |
| 4,633,874 A | 1/1987 | Chow et al. | |
| 4,655,216 A | 4/1987 | Tischer | |
| 4,671,274 A | 6/1987 | Sorochenko | |
| 4,691,703 A | 9/1987 | Auth et al. | |
| 4,763,669 A | 8/1988 | Jaeger | |
| 4,785,807 A | 11/1988 | Blanch | |
| 4,848,337 A | 7/1989 | Shaw et al. | |
| 4,850,353 A | 7/1989 | Stasz et al. | |
| 4,887,612 A | 12/1989 | Esser et al. | |
| 4,930,494 A | 6/1990 | Takehana et al. | |
| 4,940,468 A | 7/1990 | Petillo | |
| 4,958,539 A | 9/1990 | Stasz et al. | |
| 4,969,885 A | 11/1990 | Farin | |
| 4,985,030 A | 1/1991 | Melzer et al. | |
| 5,009,656 A | 4/1991 | Reimels | |
| 5,057,106 A | 10/1991 | Kasevich et al. | |
| 5,057,107 A | 10/1991 | Parins et al. | |
| 5,085,659 A | 2/1992 | Rydell | |
| 5,104,025 A | 4/1992 | Main et al. | |
| 5,122,137 A | 6/1992 | Lennox | |
| 5,147,356 A | 9/1992 | Bhatta | |
| 5,147,357 A | 9/1992 | Rose et al. | |
| 5,151,102 A | 9/1992 | Kamiyama et al. | |
| 5,190,541 A | 3/1993 | Abele et al. | |
| 5,201,900 A | 4/1993 | Nardella | |
| 5,207,691 A | 5/1993 | Nardella | |
| 5,217,460 A * | 6/1993 | Knoepfler | 606/52 |
| 5,258,006 A | 11/1993 | Rydell et al. | |
| 5,267,998 A | 12/1993 | Hagen | |
| 5,269,780 A | 12/1993 | Roos | |
| 5,290,286 A | 3/1994 | Parins | |
| 5,306,280 A | 4/1994 | Bregen et al. | |
| 5,308,311 A | 5/1994 | Eggers et al. | |
| 5,324,289 A | 6/1994 | Eggers | |
| 5,336,221 A | 8/1994 | Anderson | |
| 5,360,428 A | 11/1994 | Hutchinson, Jr. | |
| 5,364,389 A | 11/1994 | Anderson | |
| 5,389,098 A | 2/1995 | Tsuruta et al. | |
| 5,395,369 A * | 3/1995 | McBrayer et al. | 606/51 |
| 5,403,312 A | 4/1995 | Yates et al. | |
| 5,417,687 A | 5/1995 | Nardella et al. | |
| 5,443,463 A | 8/1995 | Stern et al. | |
| 5,445,638 A * | 8/1995 | Rydell et al. | 606/51 |
| 5,451,224 A * | 9/1995 | Goble et al. | 606/48 |
| 5,458,598 A | 10/1995 | Feinberg et al. | |
| 5,480,397 A | 1/1996 | Eggers et al. | |
| 5,480,398 A | 1/1996 | Eggers | |
| 5,507,106 A | 4/1996 | Fox | |
| 5,529,235 A * | 6/1996 | Boiarski et al. | 227/175.1 |
| 5,531,744 A | 7/1996 | Nardella et al. | |
| 5,571,153 A | 11/1996 | Wallsten | |
| 5,573,535 A | 11/1996 | Viklund | |
| 5,593,406 A | 1/1997 | Eggers et al. | |
| 5,603,875 A | 2/1997 | Giller et al. | |
| 5,611,798 A | 3/1997 | Eggers | |
| 5,624,452 A * | 4/1997 | Yates | 606/139 |
| 5,665,100 A * | 9/1997 | Yoon | 606/170 |
| 5,674,220 A * | 10/1997 | Fox et al. | 606/51 |
| 5,693,051 A | 12/1997 | Schulze et al. | |
| 5,716,366 A * | 2/1998 | Yates | 606/139 |
| 5,735,848 A | 4/1998 | Yates et al. | |
| 5,755,717 A | 5/1998 | Yates et al. | |
| 5,766,166 A | 6/1998 | Hooven | |
| 5,776,130 A | 7/1998 | Buysse et al. | |
| 5,797,938 A | 8/1998 | Paraschal et al. | |
| 5,800,449 A * | 9/1998 | Wales | 606/172 |
| 5,807,392 A | 9/1998 | Eggers | |
| 5,833,690 A | 11/1998 | Yates et al. | |
| 5,836,874 A | 11/1998 | Swanson et al. | |
| 5,849,011 A | 12/1998 | Jones et al. | |
| 5,891,142 A | 4/1999 | Eggers et al. | |
| 5,911,719 A | 6/1999 | Eggers | |
| 5,947,984 A | 9/1999 | Whipple | |
| 6,019,758 A | 2/2000 | Slater | |
| 6,030,384 A | 2/2000 | Nezhat | |
| 6,039,733 A | 3/2000 | Buysse et al. | |
| 6,074,389 A | 6/2000 | Levine et al. | |
| 6,086,586 A | 7/2000 | Hooven | |
| 6,106,558 A | 8/2000 | Picha | |
| 6,107,699 A | 8/2000 | Swanson | |
| 6,113,598 A | 9/2000 | Baker | |
| H001904 H | 10/2000 | Yates et al. | |
| 6,132,426 A | 10/2000 | Kroll | |
| 6,139,508 A | 10/2000 | Simpson et al. | |
| 6,143,207 A | 11/2000 | Yamada et al. | |
| 6,152,923 A | 11/2000 | Ryan | |
| 6,162,220 A | 12/2000 | Nezhat | |
| 6,174,309 B1 | 1/2001 | Wrublewski et al. | |
| 6,176,857 B1 | 1/2001 | Ashley | |
| 6,179,834 B1 | 1/2001 | Buysse et al. | |
| 6,179,835 B1 | 1/2001 | Panescu et al. | |
| 6,179,837 B1 | 1/2001 | Hooven | |
| 6,187,003 B1 | 2/2001 | Buysse et al. | |
| 6,190,386 B1 | 2/2001 | Rydell | |
| 6,193,709 B1 | 2/2001 | Miyawaki et al. | |
| 6,218,928 B1 | 4/2001 | Okada et al. | |
| 6,270,497 B1 | 8/2001 | Sekino et al. | |
| 6,273,887 B1 | 8/2001 | Yamauchi et al. | |
| 6,277,117 B1 * | 8/2001 | Tetzlaff et al. | 606/48 |
| 6,281,263 B1 | 8/2001 | Evans et al. | |
| 6,296,640 B1 | 10/2001 | Wampler et al. | |
| 6,298,550 B1 | 10/2001 | Kirwan, Jr. | |
| 6,328,703 B1 | 12/2001 | Murakami | |
| 6,334,861 B1 | 1/2002 | Chandler et al. | |
| 6,350,264 B1 | 2/2002 | Hooven | |
| 6,352,536 B1 | 3/2002 | Buysse et al. | |
| 6,398,779 B1 | 6/2002 | Buysse et al. | |
| 6,409,725 B1 | 6/2002 | Khandkar et al. | |
| 6,451,018 B1 | 9/2002 | Lands et al. | |
| 6,458,127 B1 | 10/2002 | Truckai et al. | |
| 6,458,128 B1 | 10/2002 | Schulze | |
| 6,458,130 B1 | 10/2002 | Frazier et al. | |
| 6,464,702 B2 * | 10/2002 | Schulze et al. | 606/51 |
| 6,464,704 B2 * | 10/2002 | Schmaltz et al. | 606/51 |
| 6,468,275 B1 | 10/2002 | Wampler et al. | |
| 6,485,436 B1 | 11/2002 | Truckai et al. | |
| 6,500,176 B1 * | 12/2002 | Truckai et al. | 606/51 |
| 6,511,480 B1 | 1/2003 | Tetzlaff et al. | |
| 6,527,767 B2 | 3/2003 | Wang et al. | |
| 6,533,784 B2 | 3/2003 | Truckai et al. | |
| 6,554,829 B2 | 4/2003 | Schulze et al. | |
| 6,575,968 B1 | 6/2003 | Eggers et al. | |
| 6,585,735 B1 | 7/2003 | Frazier et al. | |
| 6,602,252 B2 * | 8/2003 | Mollenauer | 606/46 |
| 6,632,193 B1 | 10/2003 | Davison et al. | |
| 6,652,521 B2 | 11/2003 | Schulze | |
| 2002/0052599 A1 * | 5/2002 | Goble | 606/40 |
| 2002/0115997 A1 * | 8/2002 | Truckai et al. | 606/51 |
| 2002/0120266 A1 | 8/2002 | Truckai et al. | |
| 2002/0169392 A1 | 11/2002 | Truckai et al. | |
| 2002/0177848 A1 | 11/2002 | Truckai et al. | |
| 2003/0018327 A1 | 1/2003 | Truckai et al. | |
| 2003/0050635 A1 | 3/2003 | Truckai et al. | |

| | | | |
|---|---|---|---|
| 2003/0055417 A1 | 3/2003 | Truckai et al. | |
| 2003/0069579 A1 | 4/2003 | Truckai et al. | |
| 2003/0078573 A1 | 4/2003 | Truckai et al. | |
| 2003/0078577 A1* | 4/2003 | Truckai et al. | 606/51 |
| 2003/0078578 A1 | 4/2003 | Truckai et al. | |
| 2003/0114851 A1 | 6/2003 | Truckai et al. | |
| 2003/0125727 A1 | 7/2003 | Truckai et al. | |
| 2003/0139741 A1 | 7/2003 | Goble et al. | |
| 2003/0144652 A1 | 7/2003 | Baker et al. | |
| 2003/0220637 A1* | 11/2003 | Truckai et al. | 606/28 |

FOREIGN PATENT DOCUMENTS

| | | |
|---|---|---|
| EP | 517 244 B1 | 3/1996 |
| EP | 518 230 B1 | 5/1996 |
| FR | 2536924 A1 | 6/1984 |
| FR | 2647683 A1 | 12/1990 |
| GB | 2037167 A | 7/1980 |
| GB | 2066104 A | 7/1981 |
| GB | 2133290 A | 7/1984 |
| GB | 2161082 A | 1/1986 |
| JP | 10-033551 | 2/1998 |
| JP | 10-118092 | 5/1998 |
| JP | 2001-057302 | 2/2001 |
| JP | 2001-170069 | 6/2001 |
| SU | 342617 | 7/1972 |
| SU | 575103 | 10/1977 |
| WO | WO 93/08754 A1 | 5/1993 |
| WO | WO 94/24949 A1 | 11/1994 |
| WO | WO 94/24951 A1 | 11/1994 |
| WO | WO 00/09190 A1 | 2/2000 |

OTHER PUBLICATIONS

Corson, "Two New Laparoscopic Instruments: Bipolar Sterilizing Forceps and Uterine Manipulator," *Medical Instrumentation*, 11(1):7-8 (1977).

Nardella, "Radio Frequency Energy and Impedance Feedback," *Proc. SPIE. Catheter-Based Sensing and Imaging Technology*, 1068: 42-48 (1989).

Pacific Silk, "Designing with Silicon Synthetic Rubber" brochure, downloaded on Nov. 1, 2004, <<http//www.pacificsilk.com>>.

Vallfors et al., "Automatically Controlled Bipolar Electrocoagulation—'COA-COMP'," *Neurosurg Rev.*, 187-190 (1984).

Japanese Office Action dated Feb. 18, 2009 for corresponding patent application, Japanese Patent Application No. 2003-562406 (END6504JPPCT).

* cited by examiner

ELECTROSURGICAL INSTRUMENT WITH REPLACEABLE CARTRIDGE

CROSS-REFERENCES TO RELATED APPLICATIONS

This application claims the benefit of priority of U.S. Provisional Application Ser. No. 60/537,085, filed on Jan. 16, 2004, the full disclosure of which is incorporated herein by reference. This application is also related to co-pending U.S. patent application Ser. No. 10/351,449 filed Jan. 22, 2003 titled Electrosurgical Instrument and Method of Use, now U.S. Pat. No. 7,112,201, and U.S. patent application Ser. No. 10/443,974, filed May 22, 2003 titled Electrosurgical Working End with Replaceable Cartridges, now U.S. Pat. No. 7,041,102, both of which are fully incorporated herein by reference.

BACKGROUND OF THE INVENTION

Field of the Invention

Embodiments of the invention relate to medical devices and methods and more particularly relate to a unitary replaceable cartridge assembly for an electrosurgical forceps, the cartridge assembly carrying electrosurgical energy-delivery means together with a slidable cutting blade.

In the prior art, various energy sources such as radiofrequency (Rf) sources, ultrasound sources and lasers have been developed to coagulate, seal or join together tissue volumes in open and laparoscopic surgeries. One surgical application relates to sealing blood vessels which contain considerable fluid pressure therein. In general, no instrument working ends using any energy source have proven reliable in creating a "tissue weld" or "tissue fusion" that has very high strength immediately post-treatment. For this reason, the commercially available instruments, typically powered by Rf or ultrasound, are mostly limited to use in sealing small blood vessels and tissue masses with microvasculature therein. The prior art Rf devices also fail to provide seals with substantial strength in anatomic structures having walls with irregular or thick fibrous content, in bundles of disparate anatomic structures, in substantially thick anatomic structures, or in tissues with thick fascia layers (e.g., large diameter blood vessels).

The effect of RF waves was first reported by d'Arsonval in 1891. (see d'Arsonval, M. A., Action physiologique des courants alternatifs; *CR Soc Biol.;* 1891; 43:283-286). He described heating of tissue when the RF waves pass through living tissue. This led to the development of medical diathermy. The physical principles of tissue interaction with Rf waves was first described by Organ, who demonstrated that alternating current causes agitation of ions in the living tissue that results in frictional heat and thermal effects (see Organ, L. W., Electrophysiologic principles of radiofrequency lesion making. *Appl Neurophysiol.;* 1976; 39:69-76). A typical Rf system consists of a very high frequency (200 to 1200 KHz) alternating current generator, an Rf monopolar electrode and ground pad (a large dispersive electrode) or a bi-polar electrode arrangement, with the electrodes and targeted tissue all connected in series. In such a circuit, Rf current enters through both the electrodes with the engaged tissue functioning as a resistor component. As the Rf current alternates in directions at high frequency, tissue ions that are attempting to follow the direction of the current are agitated. Due to natural high resistivity in the living tissue, ionic agitation produces frictional heat between bi-polar electrodes in a working end. In a mono-polar electrode, because the grounding pad has a very large surface area, the electrical resistance is low at the ground pad and hence the ionic frictional heat is concentrated at mono-polar electrode.

Thus, the application of electromagnetic energy from Rf current produces thermal effects, the extent of which are dependent on temperature and Rf application duration. At a targeted temperature range between about 70° C. and 90° C., there occurs heat-induced denaturation of proteins. At any temperature above about 100° C., the tissue will vaporize and tissue carbonization can result.

In a basic jaw structure with a bi-polar electrode arrangement, each face of opposing first and second jaws comprises an electrode and Rf current flows across the captured tissue between the opposing polarity electrodes. Such prior art Rf jaws that engage opposing sides of tissue typically cannot cause uniform thermal effects in the tissue—whether the captured tissue is thin or substantially thick. As Rf energy density in tissue increases, the tissue surface becomes desiccated and resistant to additional ohmic heating. Localized tissue desiccation and charring can occur almost instantly as tissue impedance rises, which then can result in a non-uniform seal in the tissue. The typical prior art Rf jaws can cause further undesirable effects by propagating Rf density laterally from the engaged tissue thus causing unwanted collateral thermal damage.

The commercially available Rf sealing instruments typically adopt a "power adjustment" approach to attempt to control Rf flux in tissue wherein a system controller rapidly adjusts the level of total power delivered to the jaws' electrodes in response to feedback circuitry coupled to the electrodes that measures tissue impedance or electrode temperature. Another approach used in the prior art consists of jaws designs that provide spaced apart offset electrodes wherein the opposing polarity electrode portions are spaced apart by an insulator material—which may cause current to flow within an extended path through captured tissue rather than simply between opposing electrode surfaces of the first and second jaws. Electrosurgical grasping instruments having jaws with electrically-isolated electrode arrangements in cooperating jaws faces were proposed by Yates et al. in U.S. Pat. Nos. 5,403,312; 5,735,848 and 5,833,690. In general, the prior art instruments cannot reliably create high strength seals in larger arteries and veins.

BRIEF SUMMARY OF THE INVENTION

Various embodiments of the invention provide electrosurgical instrument systems assemblies and methods that utilize a novel means for modulating Rf energy application to biological tissue to create high strength thermal welds or seals in targeted tissues. In some embodiments, the system is configured to allow for a "one-step" welding-transecting procedure wherein the surgeon can contemporaneously (i) engage tissue within a jaw structure (ii) apply Rf energy to the tissue, and (iii) transect the tissue. Particular embodiments also provide systems and methods for Rf welding of tissue with a reduction or elimination of arcing and tissue desiccation.

Various embodiments also provide a jaw structure that can engage and weld tissue bundles, defined herein as bundles of disparate tissue types (e.g., fat, blood vessels, fascia, etc.). For the welding of tissue bundles, it is desirable that the jaw surfaces apply differential energy levels to each different tissue type simultaneously. Accordingly, embodiments of the invention provide an electrosurgical system that is configured to apply differential energy levels across the jaws engagement surfaces with "smart" materials without the need for complex feedback circuitry coupled to thermocouples or other sensors in the jaw structure. These and related embodiments allow for contemporaneous modulation of energy densities across the various types of tissue in the tissue bundle according to the impedance of each engaged tissue type and region.

In order to create the most effective "weld" in tissue, it is desirable that the targeted volume of tissue be uniformly elevated to the temperature needed to denature proteins therein. To create a "weld" in tissue, collagen and other protein molecules within an engaged tissue volume are desirably denatured by breaking the inter- and intra-molecular hydrogen bonds—followed by re-crosslinking on thermal relaxation to create a fused-together tissue mass. It can be easily understood that ohmic heating in tissue—if not uniform—can at best create localized spots of truly "welded" tissue. Such a non-uniformly denatured tissue volume still is "coagulated" and will prevent blood flow in small vasculature that contains little pressure. However, such non-uniformly denatured tissue will not create a seal with significant strength, for example in 2 mm. to 10 mm. arteries that contain high pressures.

Various embodiments of systems and methods of the invention relate to creating thermal "welds" or "fusion" within native tissue volumes. The alternative terms of tissue "welding" and tissue "fusion" are used interchangeably herein to describe thermal treatments of a targeted tissue volume that result in a substantially uniform fused-together tissue mass, for example in welding blood vessels that exhibit substantial burst strength immediately post-treatment. The strength of such welds is particularly useful (i) for permanently sealing blood vessels in vessel transection procedures, (ii) for welding organ margins in resection procedures, (iii) for welding other anatomic ducts wherein permanent closure is required, and also (iv) for vessel anastomosis, vessel closure or other procedures that join together anatomic structures or portions thereof. The welding or fusion of tissue as disclosed herein is to be distinguished from "coagulation", "sealing", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the affected tissue.

At the molecular level, the phenomena of truly "welding" tissue as disclosed herein may not be fully understood. However, the authors have identified the parameters at which tissue welding can be accomplished. An effective "weld" as disclosed herein results from the thermally-induced denaturation of collagen, elastin and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in "protein entanglement" as re-crosslinking or renaturation occurs to thereby cause a uniform fused-together mass.

Various embodiments of the invention provide an electrosurgical jaw structure comprising first and second opposing jaws that carry variable impedance bodies for performing one or more of the following functions: i) modulating Rf energy delivery to engaged tissue; ii) modulating energy densities in the engaged tissues; iii) controlling ohmic heating in the engaged tissue. In one embodiment, the invention provides electrosurgical jaws that use first and second energy-delivery jaw surfaces coupled in series to an Rf source that utilizes first and second variable impedance bodies in the jaw surfaces for controlling electrosurgical energy parameters such as voltage and current within engaged tissue. The electrosurgical jaws also use first and second variable impedance bodies that define different temperature-impedance curves for controlling ohmic heating of tissue.

Many embodiment also provide assemblies for use with various electrosurgical instruments such as forceps, scissors and other surgical instruments known in the art. One embodiment provides a removable assembly for use with electrosurgical forceps having a pair of opposing jaw portions. The assembly comprises a housing and a pair of electrosurgical energy-delivery elements coupled to the housing. The energy-delivery elements have opposing tissue-engagement surfaces that are removably engageable with the pair of opposing jaw portions so as to provide tissue-engagement surfaces in opposing relation to one another. The housing otherwise includes a slidable blade member for slidable actuation relative to the energy delivery elements. One or both of the energy delivery elements can be coupled to the housing using a flexible structure or coupling. Also, the blade member itself can be flexible and can include proximally or distally facing sharp edges. At least one of the energy delivery elements can include a connector for electrically coupling the element to a voltage source such as a radio frequency (Rf) voltage source.

At least one or both energy-delivery elements can have an engagement surface carrying an electrode for ohmicly heating engaged tissue. The engagement surface can also carry a temperature-responsive variable resistive body along with one or two electrodes which can be opposing polarity electrodes. In the latter configuration, the variable resistive body can be positioned intermediate the opposing polarity electrodes.

DETAILED DESCRIPTION OF THE INVENTION

Electrosurgical jaw structure with variable impedance matrices. Various embodiments of the invention provide systems, assemblies and methods to delivery energy to targeted tissue volumes in a controlled manner to thermally weld or seal targeted tissue. Particular embodiments provide assemblies to contemporaneously (i) engage tissue between paired jaws, (ii) deliver energy to the tissue, and (iii) optionally transect the tissue to provide a "one-step" welding-transecting procedure. Such one-step welding and transecting has never been considered in the prior art. Another embodiment provides a jaw structure that can engage and weld tissue bundles, defined herein as bundles of disparate tissue types (e.g., fat, blood vessels, fascia, etc.). In order to facilitate the welding of tissue bundles, the jaw surfaces can be configured to apply differential energy levels to each different tissue type simultaneously. Another embodiment provides an electrosurgical system that can apply differential energy levels across the jaws engagement surfaces with "smart" materials without the need for complex feedback circuitry coupled to thermocouples or other sensors in the jaw structure.

It has been found that very high compression of engaged tissue in combination with controlled Rf energy delivery is desirable for welding the engaged tissue volume. Additionally, it has been found that ohmic heating and partial dehydration of tissue in the process of closing the jaw structure greatly assists in the ultimate compression of tissue (particularly tissue bundles) to the desired thickness of a thin membrane, for example 0.001" to about 0.05". With the engaged tissue in membrane thickness in a controlled gap between the engagement surfaces of the jaw structure, e.g., from about 0.001" to about 0.05", the method for controlling ohmic heating in tissue can be optimized (as described below).

Figure 1:
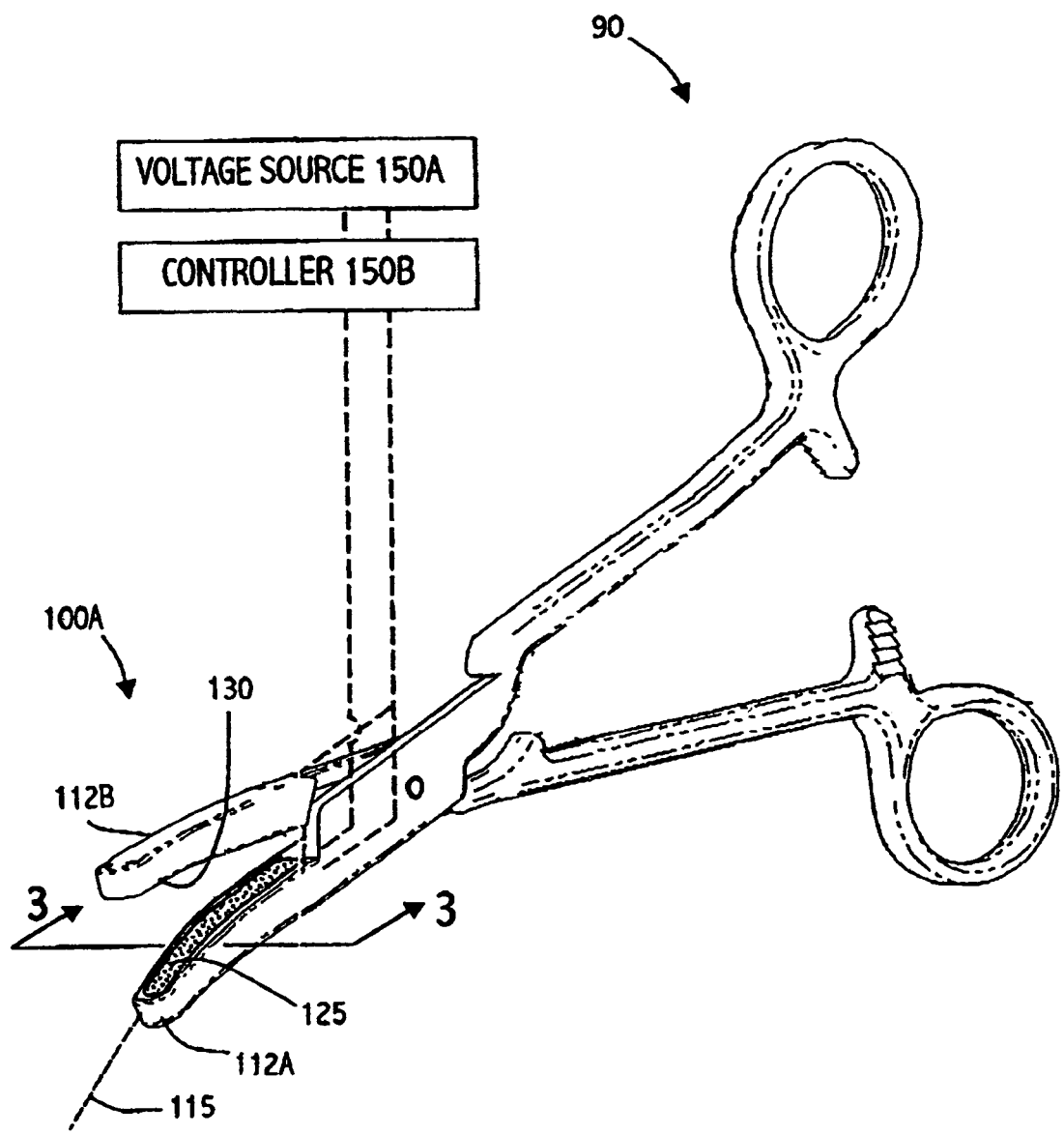
FIG. 1 is a perspective view of an exemplary surgical instrument with a jaw structure carrying variable impedance matrix bodies for tissue welding corresponding to the invention, the matrix bodies coupled to an Rf source via series and parallel circuits for modulating ohmic heating in engaged tissue.

FIG. 1 illustrates an exemplary forceps-type instrument 90 with a working end or electrosurgical jaw structure 100A corresponding to the invention that comprises first (lower) jaw element 112A and second (upper) jaw element 112B that close or approximate about axis 115 that is straight or curved. It should be appreciated that the jaw elements can have any curved or straight shape for open or endoscopic surgeries. In various embodiments, the jaws can be configured to have between about 30 to 90 degrees of curvature. In another embodiment, the jaws can actually be U-shaped or otherwise inverted. Also the jaws can have both straight and curved portions. In many embodiments, the jaws can have a scissors-type action or with one or more cam mechanisms as is known in the art. The jaws also can carry a sliding cutting blade as will be described below.

Figure 2:
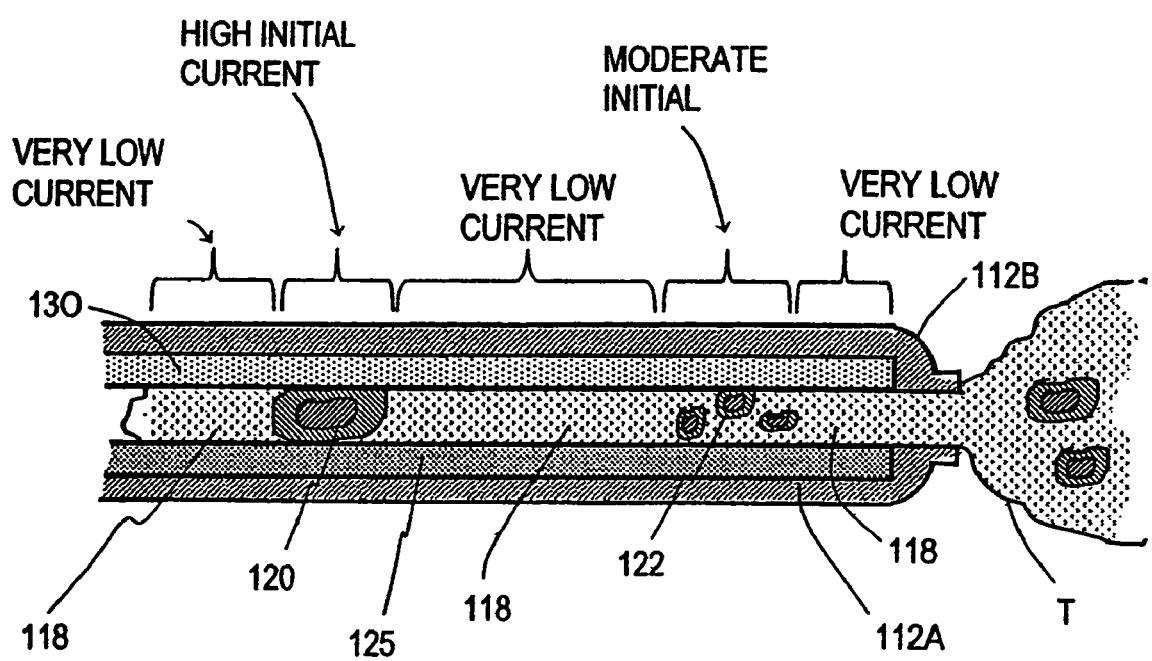
FIG. 2 is a graphic representation of opposing jaws engaging a tissue bundle comprising large blood vessels, fatty tissue and small blood vessels embedded in the fat.

Referring to FIG. 2, a discussion of the electrosurgical functionality of various embodiments of the invention will now be presented. In FIG. 2, the opposing jaws 112A and 112B are depicted schematically as engaging a tissue bundle T of differentiated tissue types—which is a common occurrence in open and endoscopic surgeries. FIG. 2 depicts a longitudinal sectional view of jaws 112A and 112B and an engaged tissue bundle T that contains, for example, insulative fat 118, large blood vessels 120 and smaller embedded blood vessels 122. The gap between the jaws is not-to-scale, and in an actual jaw structure the compressed tissue bundle T could be reduced to the thickness of a thin membrane. In an actual procedure, the tissue bundle would also contain fascia, ligamentous tissues and other tissues that would exhibit a wide range of hydration levels, electrolyte levels etc. that would locally alter tissue impedance, compressibility etc. For convenience, only three tissue types with three impedance levels are shown in FIG. 2, however these tissues are for illustrative purposes and various methods of the invention can be employed on other tissue types as well. As indicated graphically by the microcurrents MC in FIG. 2, embodiments of jaw structure 100A can be configured to contemporaneously modulate energy densities across the various types of in the tissue bundle T according to the impedance of each engaged tissue type and region. Further, it is desirable to continuously modulate energy delivery to each tissue type as the region dynamically changes in hydration, impedance and geometry. As energy is delivered, the tissue will shrink as it dehydrates.

Figure 3:
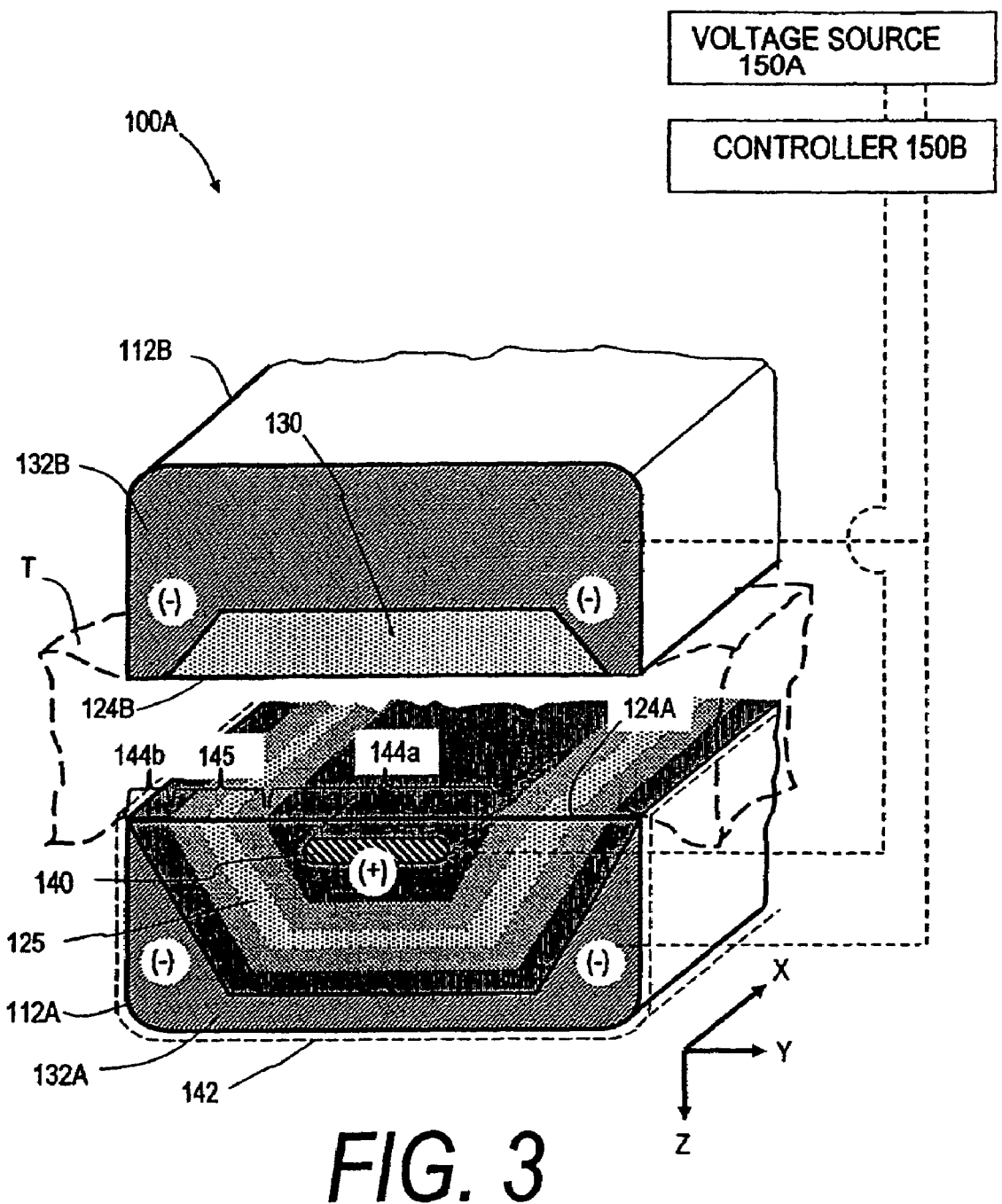
FIG. 3 is a schematic sectional view of the jaw structure of FIG. 1 taken along line 3-3 of FIG. 1 showing the variable impedance matrices in each jaw together with the series and parallel circuits.

FIG. 3 illustrates the tissue-engaging surfaces 124A and 124B of jaws 112A and 112B. Of particular interest, the jaws each carry a three-dimensional (3D) temperature-responsive variable resistive body. The lower jaw 112A carries variable impedance body indicated at 125, also at times referred to herein as a positive temperature coefficient of resistance (PTC) body or matrix. By the term three-dimensional, it is meant for example that variable impedance body 125 defines an axial dimension X and a cross-axial dimension Y about the tissue-engaging surface, as well as defining a substantial depth dimension Z that is orthogonal to the plane of the tissue-engaging surface 124A. In other words, the variable resistive body or matrix 125 has a selected thickness dimension in preferred embodiments to provide a multiplicity of varied local current flow paths through the matrix as it dynamically responds to adjacent ohmically heated tissue, as will be described below. The upper jaw 112B in one preferred embodiment shown in FIG. 3 carries a variable impedance body 130 that again can have any suitable depth dimension.

Still referring to FIG. 3, it can be seen that lower jaw 112A has a structural component or body 132A that is of a suitable electrical conductor material so that it functions as an electrode—that is indicated for convenience with a negative polarity (−). Similarly, the upper jaw 112B has structural component or body 132B that is has the same polarity (−) as the lower jaw body. An electrically conductive member or electrode 140 is provided within variable impedance matrix 125 either at the tissue-engaging surface 124A or proximate the surface as depicted in FIG. 3. Suitable electrically conductive materials include stainless steel. Both jaws optionally can have an insulative coating indicated at 142 at the exterior of lower jaw 112A. Suitable insulators include various insulative polymers known in the art.

In a preferred embodiment as in FIGS. 2 and 3, the variable impedance matrices 125 and 130 in lower jaw 112A and upper jaw 112B comprise a polyethylene or a medical grade silicone polymer that is doped with conductive particles (e.g., carbon). The use of such temperature-responsive variable impedance materials is described for related uses in co-pending U.S. patent applications: Ser. No. 10/351,449 filed Jan. 22, 2003 titled Electrosurgical Instrument and Method of Use; Ser. No. 10/032,867 filed Oct. 22, 2001 titled Electrosurgical Jaw Structure for Controlled Energy Delivery, both of which are fully incorporated herein by reference. Polymer positive temperature coefficient materials are known in the field of overcurrent protection devices that will trip and become resistive when a selected trip current and temperature is exceeded.

Figure 4A:
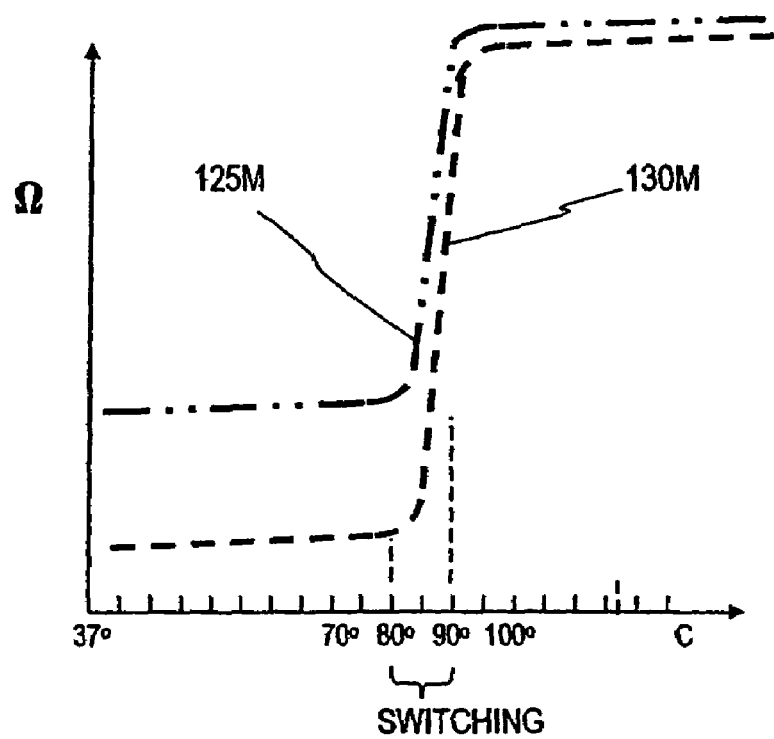
FIG. 4A is a diagram of the temperature-impedance curves of exemplary variable impedance matrix bodies as in FIG. 3.

The temperature-responsive variable impedance materials can be fabricated from a non-conductive polymer that exhibits two phases that define greater and lesser conductive states. The first phase is a crystalline or semi-crystalline state where the polymer molecules form long chains and are arranged in a more ordered architecture. When the temperature of the material is elevated, the polymer molecules maintain the crystalline architecture or structure through a selected temperature range. The polymer is designed to transition to an at least partly amorphous phase from the crystalline state at a selected temperature range. In the amorphous state, the molecules are aligned more randomly, and there may be slight changes in material geometry at the macroscale. The non-conductive polymer is combined with a dispersed, highly conductive particles (e.g., carbon micro- or nanoparticles) to form a matrix. In the crystalline phase of the polymer, the carbon particles are packed into the crystalline boundaries and form many conductive paths across and through the matrix material. In this low temperature crystalline state, the polymer-carbon matrix is engineered to have a low resistance. FIG. 4A illustrates the positively-sloped impedance-temperature curve 130M of an exemplary variable impedance matrix 130 of FIG. 3.

Various embodiments of the electrosurgical jaw structure of the invention, such as jaw structure 100A shown in FIG. 3, are configured to engage tissue and apply Rf energy to the engaged tissue T to cause ohmic heating therein. After the tissue is elevated in temperature, heat is conducted from the engaged tissue T back to the variable impedance matrices 125 and 130 to thereby elevate temperatures in at least surfaces region of the matrices 125 and 130. Details of the actual method of using the matrices to provide high temperature and low temperature process limits are described below. As long as the temperature increase in the matrix portion adjacent the ohmically heated tissue does not cause a phase change in the polymer, current can flow unimpeded through the matrix. When the temperature of the matrix material is elevated to a selected temperature, called herein a switching range, the temperature will cause a phase change in the polymer (see FIG. 4A). The crystalline structure of the polymer will disappear, the polymer volume may expand very slightly, and the carbon chains that allow conduction across the matrix will be broken—resulting in an extraordinary increase in resistance. The polymer-carbon matrix can define a resistance measured in milliohms or ohms before the phase change. After the phase change, the matrix' resistance can be measured in megaohms. Current flow can be reduced accordingly, or terminated, which is used in particular manners corresponding to the invention to precisely control Rf energy densities in the engaged tissue.

The process described above is reversible so that when an affected portion of a matrix falls in temperature, the polymer component will return to its crystalline structure and that particular matrix volume will return its original state. The conductive carbon particles will reform into conductive paths within the interstices of the crystalline polymer architecture. It has been found that the variable impedance body, for example body 130 in the upper jaw, can spatially modulate Rf current flows in a dynamic manner wherein micron scale regions are conductive and adjacent micron scale regions are non-conductive in response to the temperature of engaged tissue. In this way, the invention provides a means for spatially modulating Rf current flow, and thus energy delivery, on a micron or other highly precise scale.

As the temperature of the matrix falls, it appears that the exact same conductive paths may not exactly reform themselves after first use of the matrix, and for this reason the polymer matrices of the invention may be temperature cycled several times in the fabrication process which appears to cause the material to have substantially resettable conductive paths. In the fabrication process, the matrix can also be treated in various processes (e.g., gamma, UV irradiation etc.) to cross-link the polymer or co-polymers of the matrix.

Figure 4B:
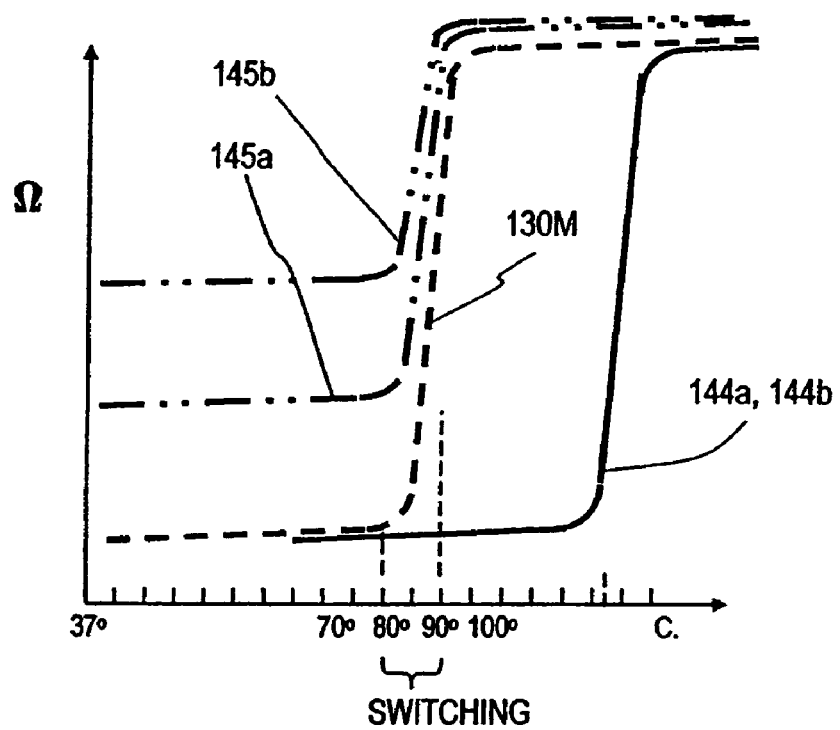
FIG. 4B is a diagram similar to that of FIG. 4A illustrating alternative temperature-impedance curves of variable impedance matrix bodies.

Referring again to FIG. 3, in one embodiment polymer matrix 125 has at least two differentiated regions 144 and 145 that define different temperature-impedance curves as illustrated in FIG. 4B. The regions 144a and 144b (collectively 144) at the center of the lower jaw and the laterally-outward edge of the jaw are of a highly conductive matrix that will only terminate current flow therethrough at a high temperature, for example between 100° C. and 200° C. as shown in FIG. 4B. These regions 144 effectively function as the opposing polarity conductive electrodes as the regions 144 are in contact with the central first polarity conductor 140 and the second polarity jaw body 132A. The lower jaw's matrix region 145 can also provide a plurality of slightly different regions 145a and 145b that have somewhat different base resistances and/or switching ranges as shown in FIG. 4B for reasons described below. Consequently, matrix region 145 can have a base resistance that is somewhat higher than that of matrix 130 in the upper jaw 112B. The jaw structure is coupled to voltage source 150A (a radiofrequency generator) and controller 150B for controlling duration of energy delivery and other Rf parameters such as power, total delivered energy, etc. (see FIG. 3). The manner in which matrices 125 and 130 operate to modulate energy densities in tissue will be described in greater detail below.

Figure 5:
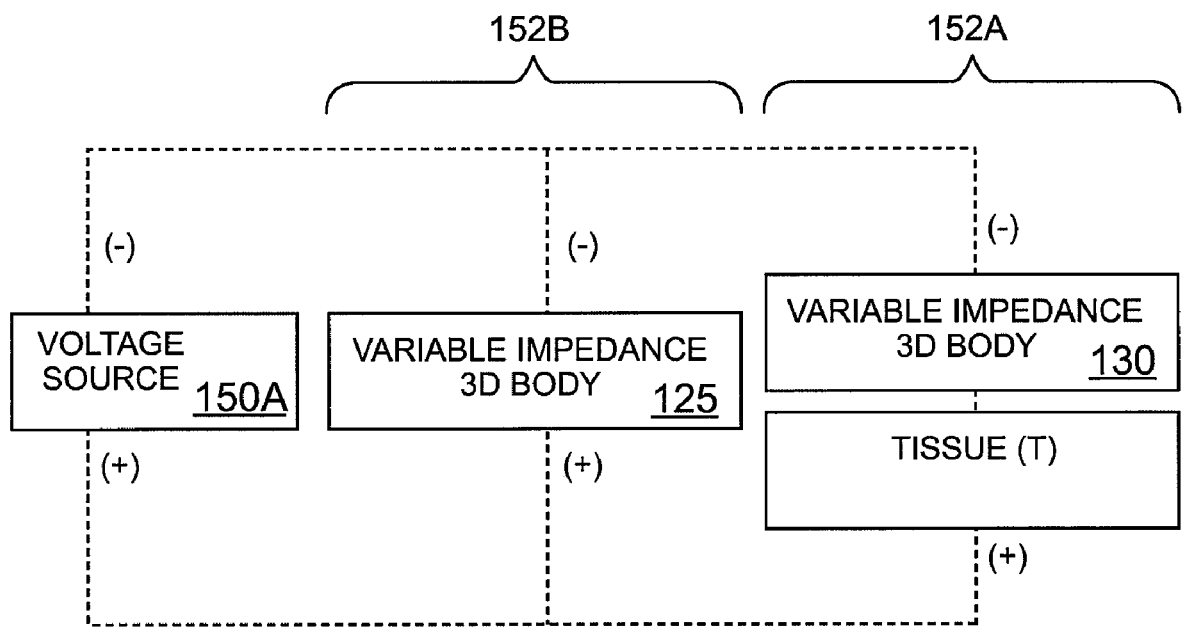
FIG. 5 is a block diagram of the series and parallel electrical circuit components of the working end of FIG. 3.

In particular embodiments, jaw structure 100A can be configured to utilize the two differently performing matrices 125 and 130 (FIG. 3) in combination with the series and parallel circuitry of FIG. 5 to provide effective high and low process limits for temperatures and energy densities in the engaged tissue T. It has been found that such dynamic energy and temperature controls are optimal for creating uniform thermal effects in tissue to denature tissue proteins and to create high strength welds. In one embodiment as in FIG. 3, the matrix 130 in upper jaw 112B is configured (e.g., by selection of material composition, process etc) to exhibit unique temperature-impedance characteristics represented by the positively-sloped curve 130M of FIG. 4B. This matrix 130 maintains a relatively low base resistance over a selected base temperature range with a significant increase in resistance above a selected narrow temperature range (switching range) that can be any 1° to 10° range between about 50° C. and 200° C., and more preferably between about 70° C. and 120° C. In comparison, the matrix region 145 in lower jaw 112A is configured to have an impedance-resistance curve exhibiting a higher initial base resistance (see FIG. 4B). The matrix region 145 provides this higher base resistance over a similar temperature range as matrix 130. The matrix 145 and its temperature-impedance curves (145a, 145b) in FIG. 4B again exhibits a significantly increasing resistance above its selected switching range, which can fall in the range described previously with reference to matrix 130.

Figure 6A:
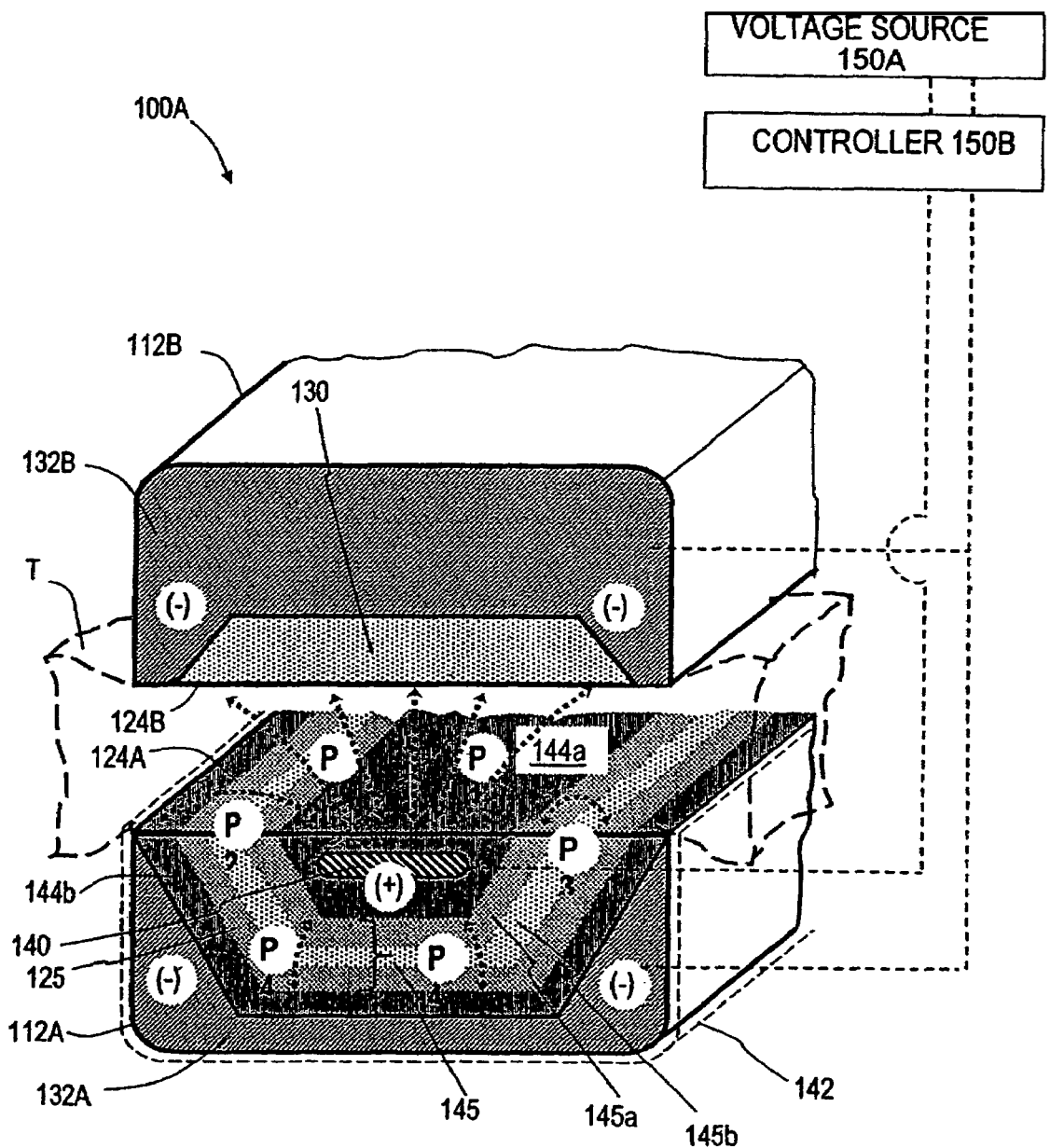
FIG. 6A is a sectional schematic view of the variable impedance matrix bodies showing potential current flow paths in the engaged tissue and the matrix bodies.

FIG. 6A schematically depicts the manner in which the jaw structure 100A of FIGS. 1 and 3 can self-modulate current flow among multiple paths—depending on the temperature of the engaged tissue and other electrical conduction parameters of the tissue to which the matrices 125 and 130 respond. FIG. 6A depicts a sectional view of the jaws 112A and 112B as in FIG. 3 engaging tissue T in phantom view. In FIG. 6A, the tissue thickness is not to scale to allow a graphic representation of potential current paths. In actual operation, the working end 100A of FIG. 6A has the ability to modulate current flow among multiple different paths through the tissue T as well as through the matrices 125 and 130. Also, both current and voltage can be modulated among multiple current paths. Current and voltage in the tissue T is modulated after the tissue is ohmically heated—and thereafter the tissue T transfers heat by passive conduction to adjacent regions of matrices 125 and 130. While there will exist a multiplicity of potential current paths in the engaged tissue and matrices, FIG. 6A, and FIGS. 10A-10D, illustrate in a simplified jaw, four generally different flow paths, P1 through P4, that effectively describe the general types of current flow paths that come into play in a self-modulating Rf ohmic heating method of the invention. The flow paths P1 through P4 do not indicate that current flows are dynamic and can be localized (conductive or non-conductive) across micron scale regions of the engagement surface of the matrices as is discussed herein.

The timing and potential switching between current paths during operation is described in more detail below.

Figure 6B:
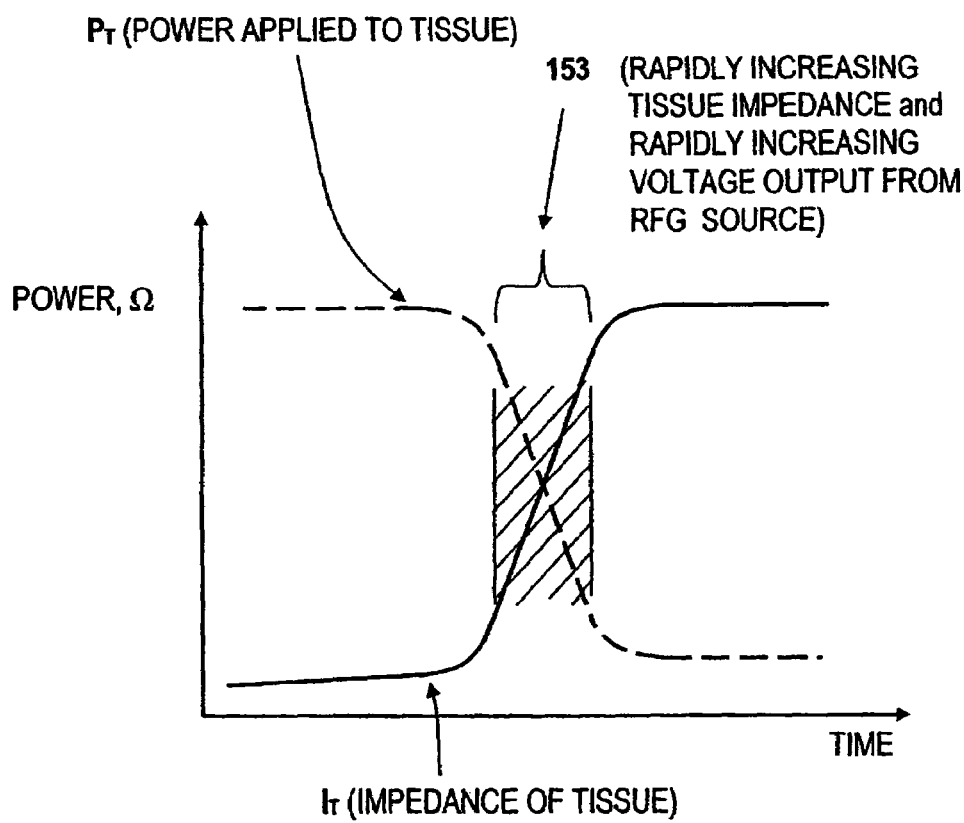
FIG. 6B is a graph illustrating power and impedance curves that illustrates feature of the invention.

Further, FIG. 6B graphically depicts operational characteristics of an embodiment of a method of the invention, wherein Rf energy application to the engaged tissue is illustrated over a selected time interval. The horizontal axis indicates elapsed "time" after initiation of Rf energy delivery and ohmic heating, while the vertical axis indicates impedance ($\Omega$) or power (P) for various curves. The curve marked $I_T$ represents the impedance of the engaged tissue over time. The curve marked $P_T$ represents the power (function of voltage and current) that is applied to the engaged tissue over time. As can be seen in FIG. 6B, after tissue is initially engaged and Rf energy is applied, the impedance of the tissue ($I_T$) remains low at a base level for an initial period, and power applied ($P_T$) to the engaged tissue is high for the corresponding time interval. In terms of schematic current flow paths in tissue, this initial rapid, high power ohmic tissue heating is generally represented by flow paths P1 (and to some extent path P2) in FIG. 6A. In other words, substantial RF energy densities are created in the tissue as current flows between electrode 140 and opposing jaw body 132B through the multiplicity of conductive paths in the variable resistive body 130. In terms of the circuitry of the working end, referring to FIG. 5, the high current flow occurs in the (first) series component indicated at 152A that engages the tissue. It is during this time interval, that may be only a fraction of a second (e.g. 0.01 to 0.5 seconds) to several seconds, that the temperature-responsive variable resistive body 130 in the upper jaw plays its major current limiting role in spatially modulating Rf paths in the highly compressed tissue to cause substantially uniform ohmic heating over the engagement surfaces and within adjacent tissue regions.

Referring back to FIG. 6B, as the tissue impedance rises in curve $I_T$, a critical time interval is reached (indicated at 153; hatched area) wherein tissue desiccation and potential arcing are possible—which in turn, would cause potential tissue carbonization and destroy, reduce or eliminate weld strength. Commercially available Rf devices with feedback power control typically cause tissue desiccation and charring with resulting detrimental effects on weld strength. The feedback mechanisms, such as a thermocouple or impedance monitoring, cannot respond rapidly enough and also cannot provide a spatial response to direct current flow away from only the desiccated tissue. At the same time that tissue impedance rises, there is a rapid increase in voltage output from the generating source in this initial period after the source 150A is turned on. It is at this time that the temperature-responsive variable resistive body 125 in the lower jaw 112A plays its voltage or power limiting role to prevent or reduce potential arcs in the lowered-impedance tissue. The potential arcs in the tissue would occur principally in flow path P2 (and related path P3) wherein opposing polarity conductive portions are in closest proximity. In various embodiments, the engagement surface and circuitry are configured to automatically limit power—to insure that an arc does not occur. This is accomplished by the placement of variable resistive body 125 in lower jaw 112A to allow current to flow in paths P4 directly between the opposing polarity body portions at an interior region of the jaw—and not within the tissue. Thus in use, the placement of variable resistance body 125 in lower jaw 112A provides a means for preventing or reducing arcing during the welding process which in return results in a more uniform and higher strength weld.

In terms of the circuitry of the working end, referring again to FIG. 5, this subsequent current flow for prevention of arcs occurs in the (second) parallel component indicated at 152B.

It can easily be understood that current flow is then modulated between the first and second circuit components 152A and 152B (FIG. 5) which, in turn, depends on the temperature (and hence impedance) of variable resistive body 130 (see FIG. 5) in the first circuit component 152A. Referring back to FIG. 6B, it can be seen that the power-to-tissue curve ($P_T$) drops to a low level when the tissue is welded since the energy is directed through the second circuit component 152B (FIG. 5). It should be appreciated that the power and impedance curves of FIG. 6B are a graphic generalization, and each micron scale region tissue would be represented by an independent set of power and impedance curves at any instant in time. For example, FIG. 10D illustrates that different spaced apart regions of engagement surfaces modulate current flow differently—depending on highly localized temperature and compression parameters of the engaged tissue.

In FIG. 6A, flow paths P1 indicates potential Rf microcurrent flows directly through tissue T between first polarity electrode 140 and conductive region 145 and the low resistance matrix 130 of upper jaw 112B that overlies the (opposing) second polarity jaw body 132B. It can be understood that these current paths P1 provide initial rapid ohmic heating of tissue. Flow paths P2 indicate Rf current flow through tissue T between the highly conductive regions 144a and 144b that are laterally spaced apart in the lower jaw that are in contact with first polarity conductor 140 and second polarity jaw body 132A, respectively.

Of particular interest, potential current flow paths indicated at P3 and P4 are unique to embodiments of the invention and come operate to modulate ohmic heating in engaged tissue as its conductive parameters (impedance, temperature, and hydration) are dynamic during energy application. Potential flow paths P3 represent potential microcurrent paths through a region of tissue between spaced apart surface portions of matrix 125 that engage such a tissue region. Potential current flow paths P4 occur at an interior of the jaw and the 3D matrix 125 wherein current can flow for voltage limiting purposes from electrode 140 across the matrix region 145 to the interior of the opposing polarity jaw body 132A. A more detailed step-by-step description of current flow is provided below.

For clarity of explanation, FIG. 6A depicts the principles of the working end in a basic forceps-type jaw structure 100A of FIGS. 1 and 3. It should be appreciated that the same variable impedance matrices 125 and 130 can be provided in a jaw structure indicated at 100B in FIGS. 7 and 8 that is configured to carry a blade for transecting the welded tissue. Further, the same variable impedance matrices 125 and 130 can be carried in a one-step jaw structure that is described below (FIGS. 11-12) wherein jaw closing, Rf energy delivery and tissue transection occur in a single operation. Now referring to FIGS. 7 and 8, a forceps-type instrument is shown with a detachable cartridge 154 that carries a thin flexible blade member 155 that can be pushed by thumb slider 156 when the jaws are locked in a closed position. Such a blade cartridge was disclosed in co-pending U.S. patent application Ser. No. 10/443,974, filed May 22, 2003 titled Electrosurgical Working End with Replaceable Cartridges which is incorporated herein by this reference.

Figure 7:
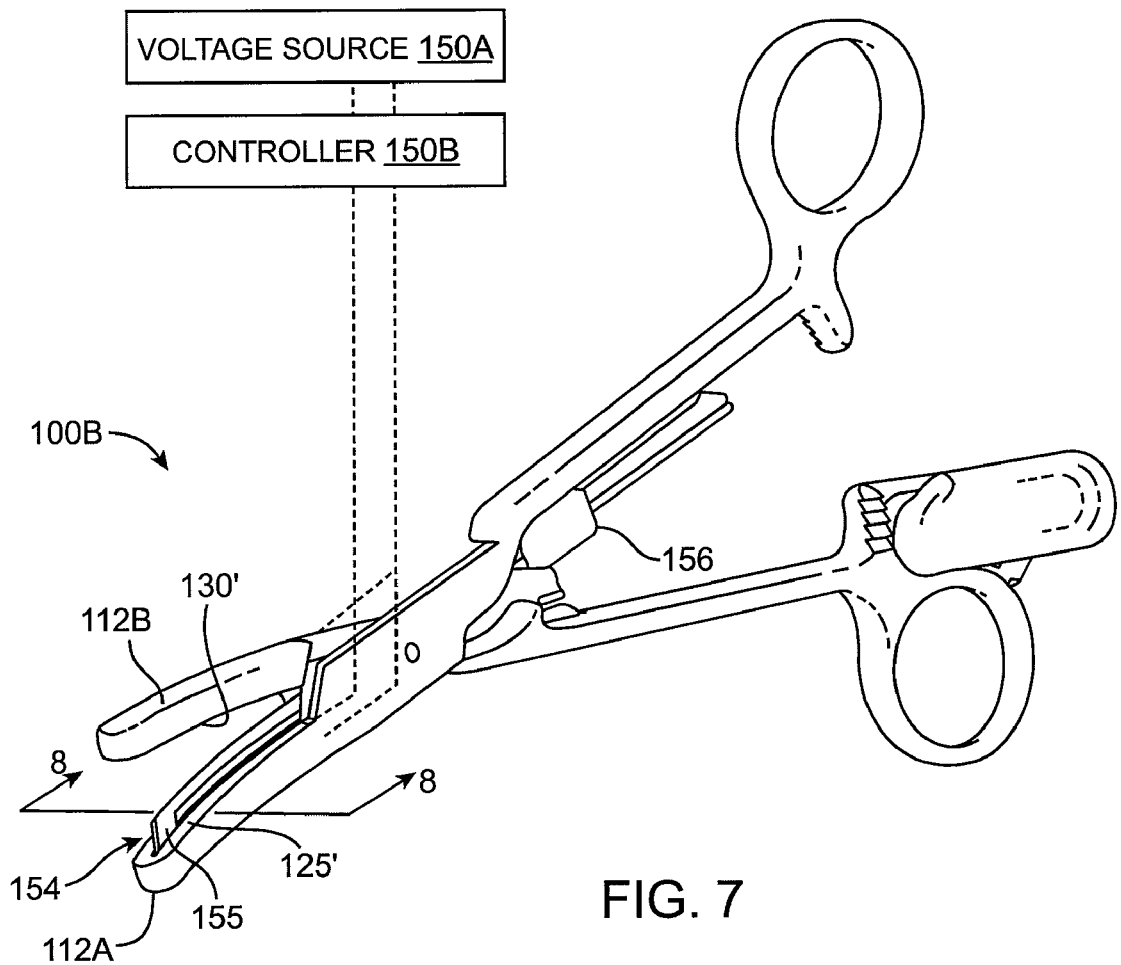
FIG. 7 is a perspective view of an alternative instrument with a jaw structure carrying variable impedance matrix bodies together with blade means for transecting tissue.
Figure 8:
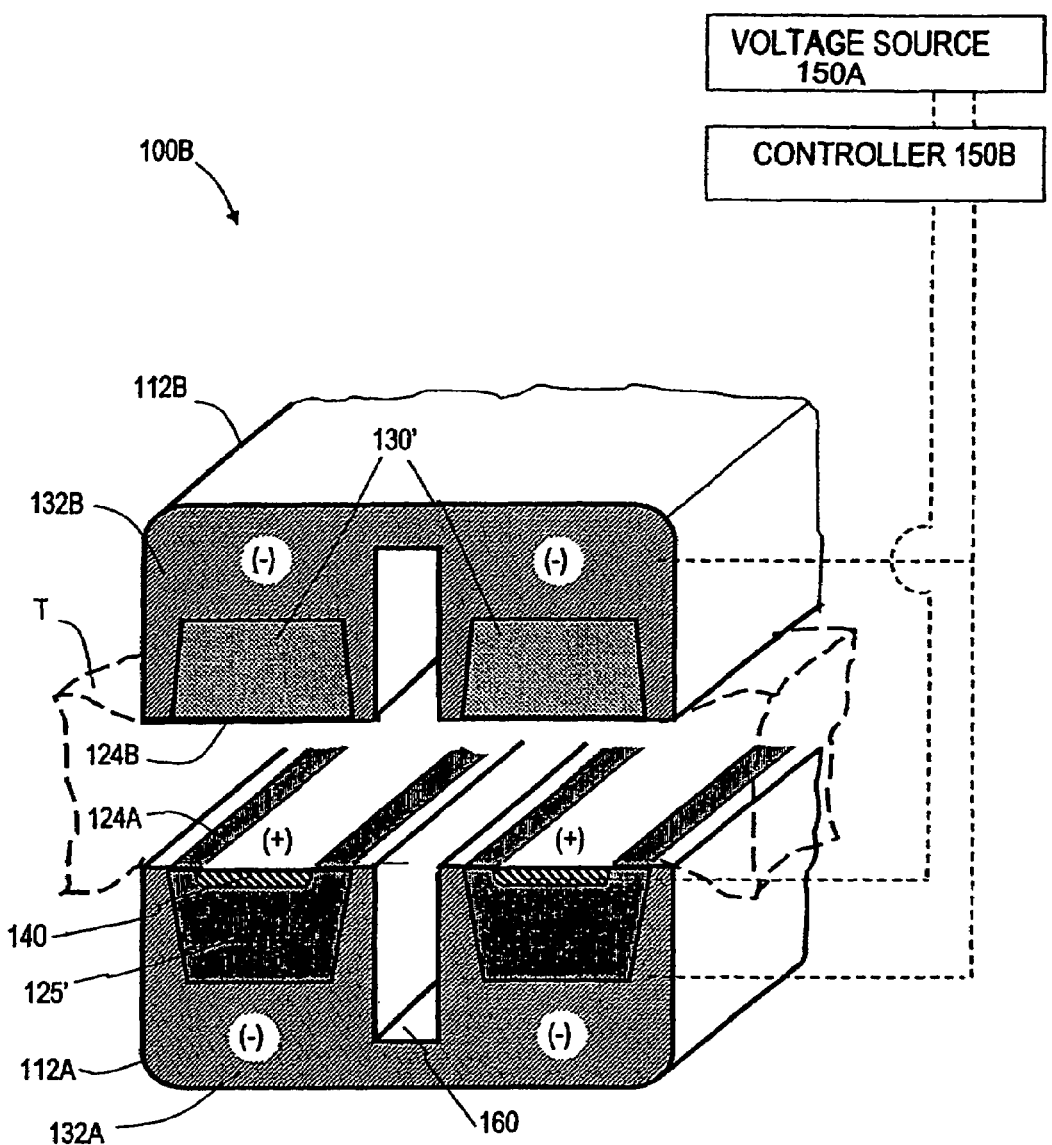
FIG. 8 is a sectional view of the jaw structure of FIG. 7 taken along line 8-8 of FIG. 7 showing the variable impedance matrices in each jaw together blade means.

FIG. 8 illustrates a cross section of the upper and lower jaws 112A and 112B with a central blade slot 160 for receiving the slidable, flexible blade member 155. The jaw bodies can carry variable impedance matrices 125' and 130 on either side of the blade slot 160. Matrices 125' and 130 can be similar (or identical) to the matrices depicted in FIG. 3. In the exemplary embodiment of FIG. 8, the lower jaw 112B has a matrix 125' that is simplified in that electrode 140 is exposed in the center of the jaw's engagement surface 124A with a portion of the 3D matrix 125' extending laterally on either side of blade slot 160 as well as within the interior of the jaw. As can be seen in FIG. 7, matrix extends in a "U"-shape around the end of blade slot 160 to allow welding of engaged tissue around the end of a welded and transected tissue region.

Figure 9:
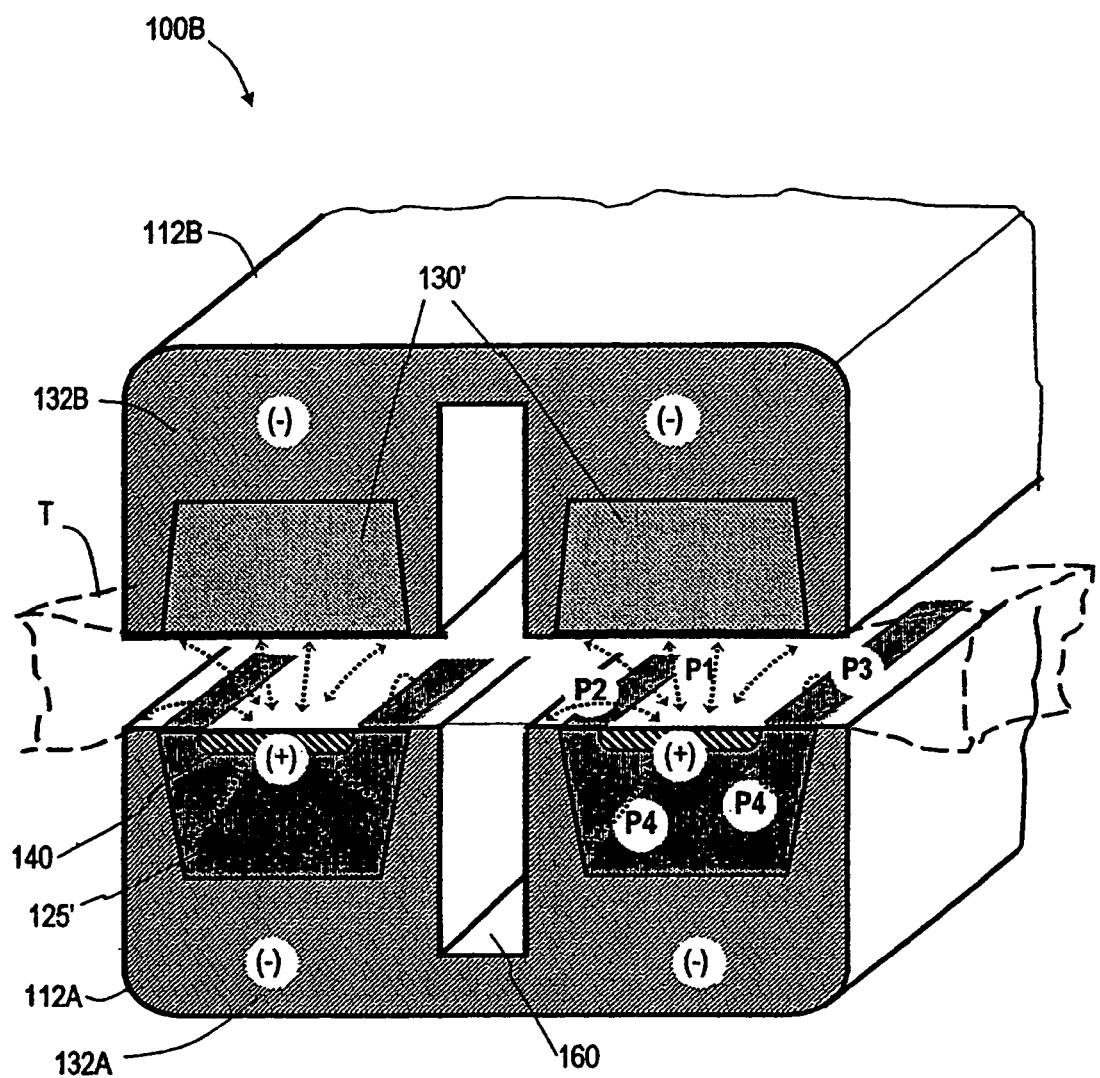
FIG. 9 is a sectional schematic view of the jaw structure of FIGS. 7-8 that illustrates potential current flow paths in the engaged tissue and the matrix bodies.

The working end 100B of FIGS. 7-8 functions to modulate Rf energy application to tissue between multiple potential paths as described above and depicted in FIG. 6A. FIG. 9 illustrates the working end 100B of FIGS. 7-8 and again graphically depicts the potential Rf current paths in tissue and across regions of the variable impedance matrices. The current paths P1, P2 and P3 again represent potential paths in the engaged tissue T. In FIG. 9, the current paths P4 represent paths within the interior regions of matrix 125' between first polarity (+) surface conductor 140 and a second polarity (−) region of jaw body 132A.

2. Method of utilizing temperature responsive variable impedance matrices for Rf modulation. Now turning to FIGS. 10A-10D, the sequential energy delivery phases of various embodiments of method of the invention are graphically illustrated. In FIGS. 10A-10D, the opposing jaws 112A and 112B are depicted engaging a tissue bundle T, and Rf energy application to tissue is modulated by matrices 125 and 130 between various paths P1-P4 in the tissue to create a uniform temperature without desiccation or charring to provide an effective high strength weld. FIGS. 10A-10D illustrate a basic jaw structure 100C similar to that of FIGS. 7-8 without a blade member, but it should be appreciated that a jaw 100B with a reciprocatable blade as in FIGS. 7-8 would create a weld by the same means of energy application and modulation. For clarity of explanation, the engagement surface 124A of FIGS. 10A-10D has the central conductive member or electrode 140 exposed in the surface (cf. FIGS. 7-9).

Figure 10A:
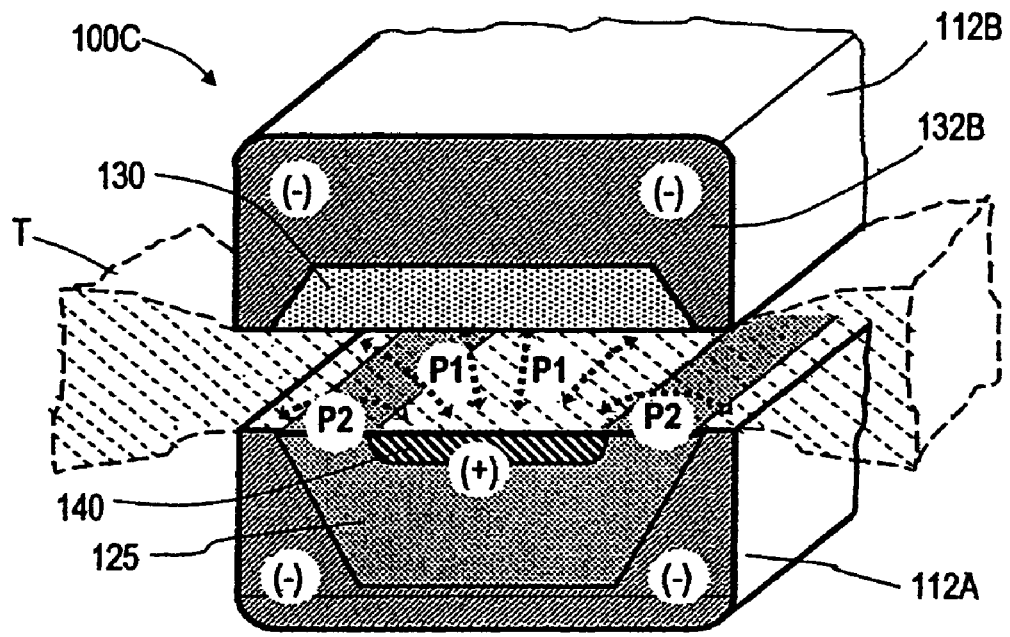
FIG. 10A is a sectional view of the jaw structure of FIGS. 7-8 illustrating an initial step in a method of the invention wherein Rf current flow paths cross the engaged tissue to cause ohmic heating therein.

Now turning to FIG. 10A, an initial energy application step is illustrated wherein tissue bundle T is engaged as the jaws apply compression and the surgeon applies Rf energy to the tissue. At initiation of Rf energy application, FIG. 10A illustrates that current flows are substantially through the tissue between the first polarity conductor 140 and the opposing matrix 130 and laterally-outward upper jaw 132B as well to the second polarity lower jaw body 132A, that is in paths P1 and P2 as depicted in FIGS. 3 and 9. Thus, FIG. 10A depicts current flow that causes very high energy densities and very rapid ohmic heating in the engaged tissue T. In this initial phase of Rf energy application to the jaw structure 100C and to the engaged tissue T, the matrices 125 and 130 are, in effect, in a stand-by mode and are not yet operating to modulate flow paths of the microcurrents in the tissue. The matrix 130 in the upper jaw at ambient room temperature has a low base resistance (see FIG. 4B) and allows a multiplicity of conductive flow paths all across and through the matrix 130 to the second polarity jaw body 132B from the first polarity conductor 140 in the lower jaw through the tissue T.

In FIG. 10A, the ohmically heated tissue causes conductive heat transfer to the matrices 125 and 130 to heat at least the surface regions of both matrices. At the same time (see FIG. 10B) the ohmically heated tissue T dehydrates, changes its geometry by shrinking and exhibits an increased impedance. In this phase of energy application, the variable impedance matrix 130 responds according to its selected temperature-impedance curve (see e.g., FIG. 4B) wherein the material regulate and modulate flow paths P1 of microcurrents therethrough. For example, the switching range of the matrix can be between about 60° C. to 120° C. and is more preferably in the 70° C. to 90° C., range. During and following this phase, the impedance of tissue regions will be substantially matched by the induced impedance of adjacent regions of matrix 130, to thereby modulate current flow in paths P1 between the jaws. At the same time, the matrix 130 will prevent any possibility of arcs or sparks at the interface of a jaw surfaces 124A and 124B with the engaged tissue since current flow will be eliminated before excessive high temperatures are reached about any region of the tissue-jaw interfaces. The prevention of such arcs eliminates the possibility of unwanted tissue charring.

During this initial energy application phase, the ohmically heated tissue also will conduct heat back to matrix 125 in the lower jaw 112A to elevate the lower matrix above its selected switching range, for example in the 70° C. to 90° C., range. Still referring to FIG. 10A, as the thickness of tissue T is reduced by compression and ohmic-heating induced dehydration, the increased impedance of the tissue will first prevent microcurrent flows in paths P1 as the upper jaw's matrix 130 is masked. At this point, there will remain the possibility of microcurrent flows in paths P2 between the electrode 140 and the laterally-outward jaw body portion 132A.

Figure 10B:
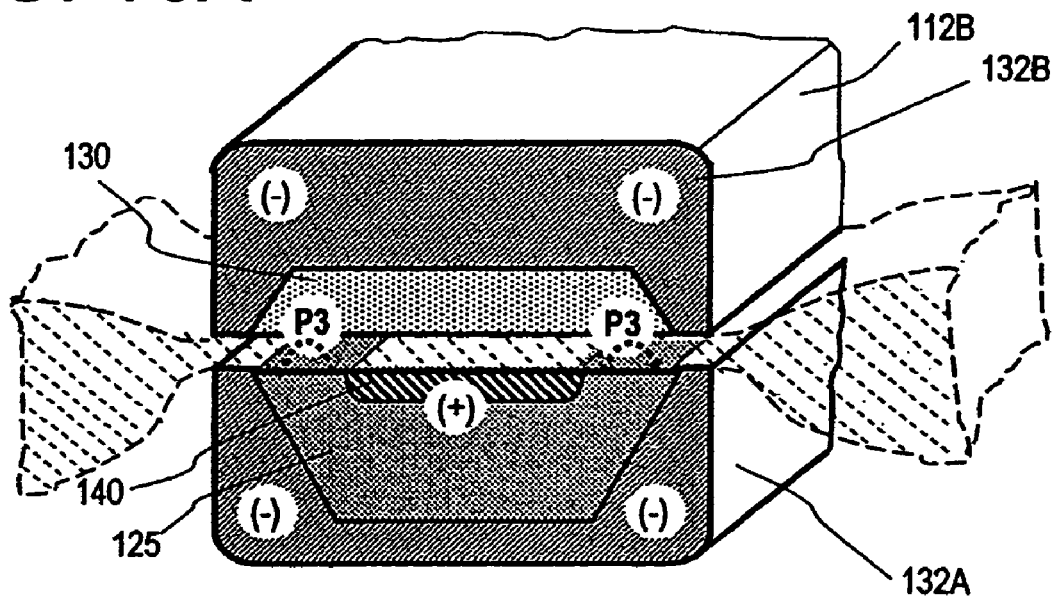
FIG. 10B is a sectional view of the jaw structure of FIG. 10A depicting a subsequent step.

Now referring to FIG. 10B, it can be seen that the dehydrated tissue T typically will be compressed to a thin membrane which can increase its impedance in the most direct paths of current (P1 and P2) between the opposing polarity body portions. With the tissue in this condition, the reduction or termination of ohmic heating will cause slight cooling of the tissue and re-hydration of the tissue can occur due to inward fluid migration. In this state, the lower matrix 125 will respond by cooling and then by causing microcurrent flows in paths P3 as indicated in FIG. 10B. Of particular interest, the increase in ohmic heating is then localized in these lateral regions of the engaged tissue while the tissue impedance still masks the upper jaw matrix 130. During this regulated phase of Rf energy application, the engaged tissue may hydrates to allow current flows in paths P1 and P2 to cause additional ohmic tissue heating. Thus, it can be understood how the temperature responsive matrices operate to self-modulate ohmic energy densities in the tissue between the various potential flow paths.

Figure 10C:
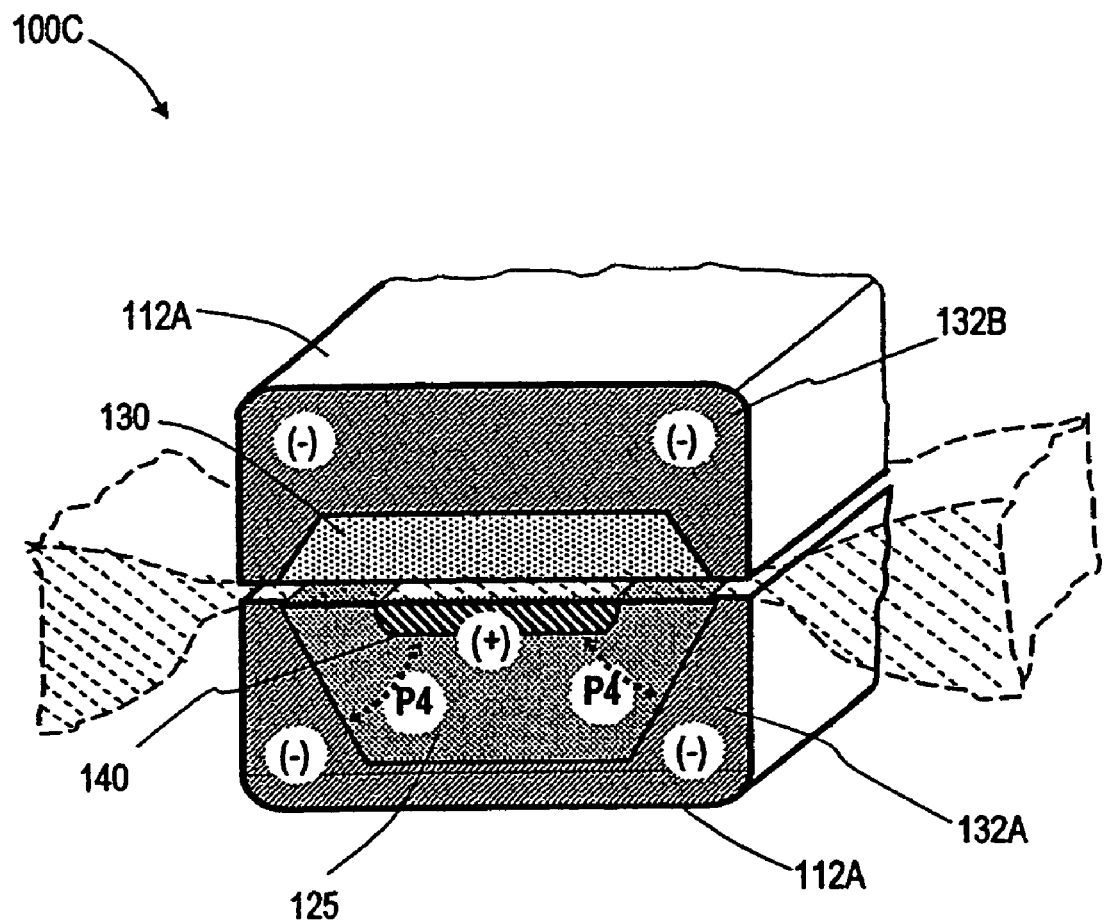
FIG. 10C is another sectional view similar to FIGS. 10A-10B depicting a step in a method of the invention wherein Rf current flow paths within an interior of a variable impedance matrix prevent sparking at a jaw engagement surface.
Figure 10D:
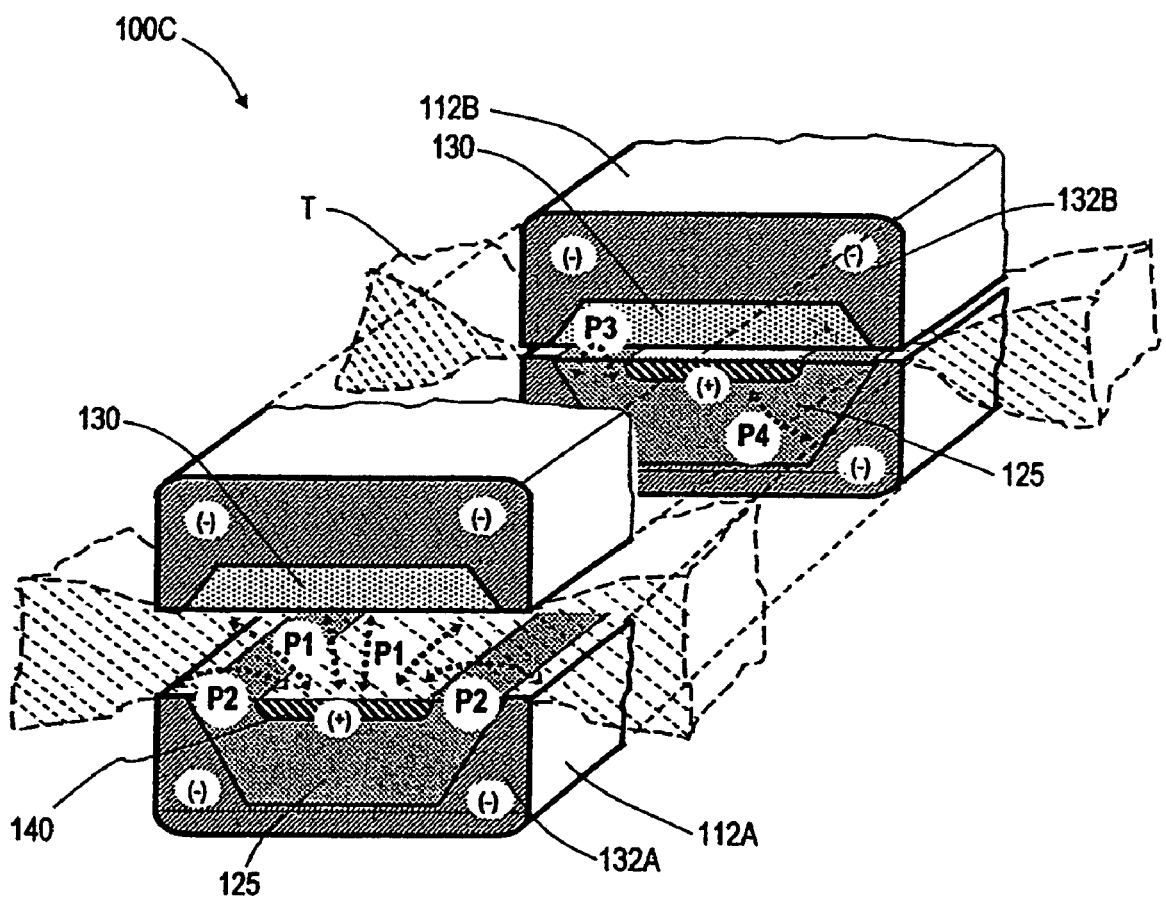
FIG. 10D is another view similar to FIGS. 10A-10C depicting a step in a method of the invention wherein Rf current flow paths occur in different axial regions of the jaws depending on local jaw compression.

FIG. 10C indicates another potential flow path P4 that can come into play if any voltage occurs that could cause an arc at the jaw-tissue interface. In effect, the energy can be dissipated by energy flows in the paths indicated at P4 between the first polarity conductor 140 and the second polarity lower jaw body 132A directly through the lower matrix 125 at the jaw's interior.

FIGS. 10A-10C indicate generally how the temperature-responsive matrices 125 and 130, at the tissue-engaging surfaces 124A and 124B, will modulate ohmic heating in the engaged adjacent tissue T. It should be appreciated that the energy modulation also occurs about very localized regions of the engaged tissue T that is made up of different tissue types as discussed in the text accompanying FIG. 2. Thus as any local region of tissue impedance changes during ohmic heating, the local adjacent region of matrix 130 in the initial phase will move to an impedance matching level. In this way, matrix 130 operates to modulate Rf energy delivery and thus ohmic heating of engaged tissue T.

Further, as described above, the tissue dimensions and geometry between the engagement surfaces 124A and 125B of the jaws is dynamic partially as a result of the shrinking that can occur during ohmic heating of the tissue T. Thus, the local dynamics of ohmic heating in tissue along the axial length of the jaw can be significant. FIG. 10D illustrates the pivoting jaw structure 100C as applying higher compression to more proximal tissue regions as the jaws close and the tissue dehydrates and shrinks during energy delivery. It can be understood that ohmic heating is thus modulated by matrices 125 and 130 in the jaws' engagement surfaces to provide locally independent energy densities in discrete tissue regions depending on local tissue temperature and impedance—as well as tissue geometry.

It has been found that the system described above can be operated with a pre-set duration of Rf energy delivery, wherein energy flow and tissue heating is self-regulated by matrices 125 and 130 to effectively provide high and low process limits for the selected duration of energy application. Depending on selected power levels and selected matrix parameters, duration of energy application to create an effective weld can range between about 1 second to 20 seconds, and more preferably is between about 3 second to 15 seconds.

Figure 11:
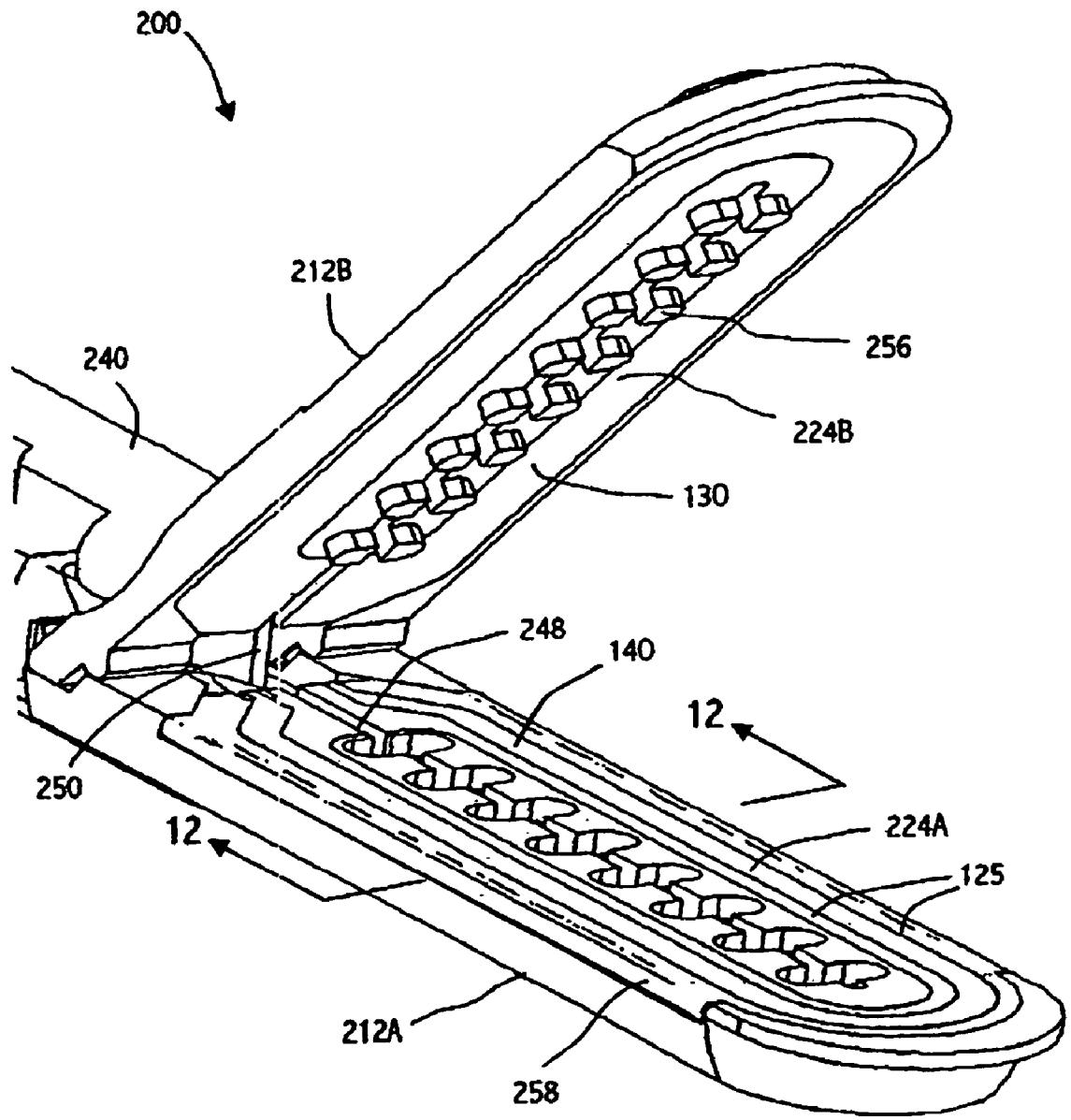
FIG. 11 is a perspective view of an alternative high-compression jaw structure carrying 3D variable impedance matrix bodies that is adapted for one-step tissue welding and transection corresponding to the invention, the matrix bodies coupled to an Rf source via series and parallel circuits.
Figure 12:
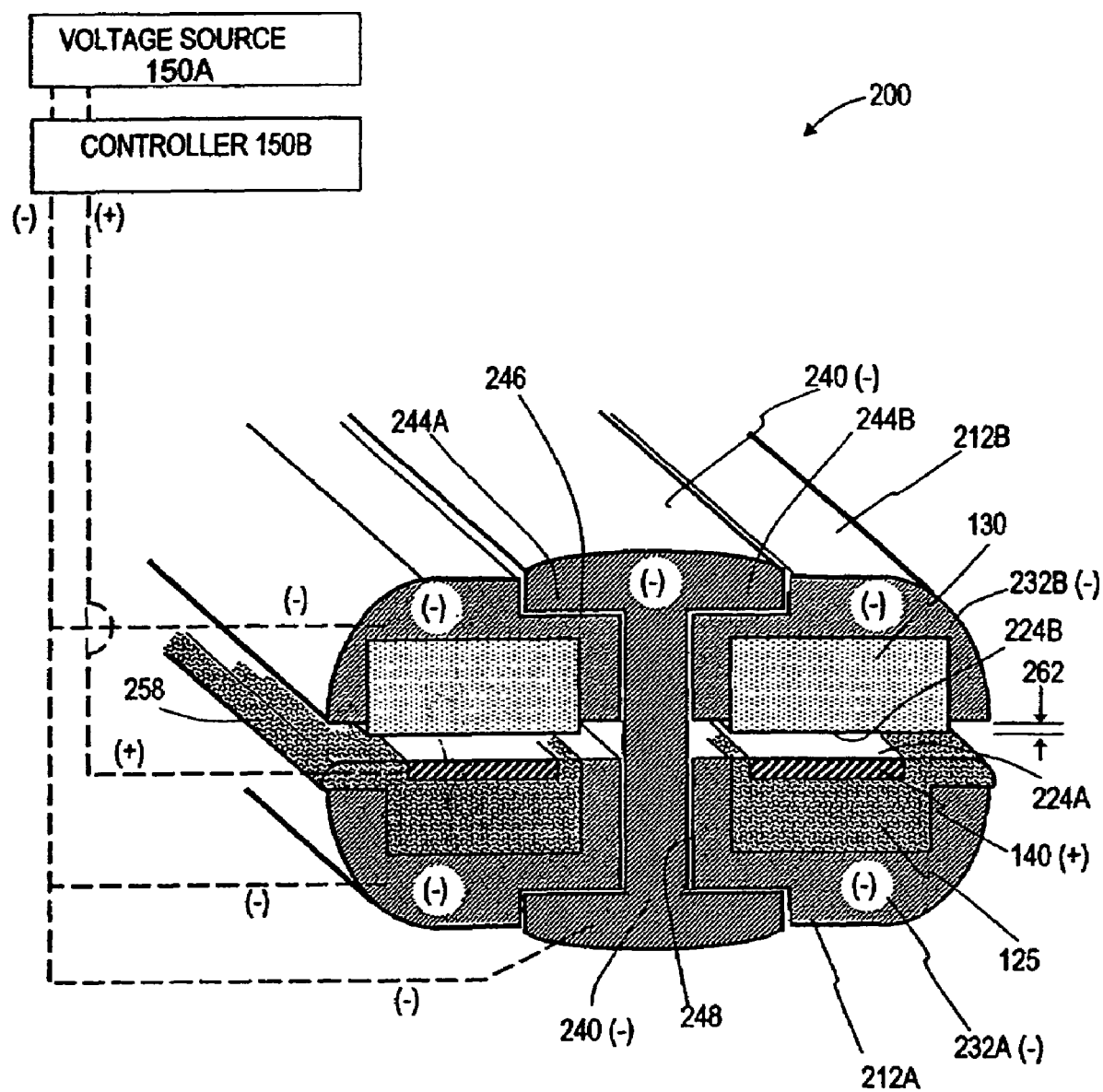
FIG. 12 is a schematic sectional view of the jaw structure of FIG. 11 taken along line 12-12 of FIG. 11 showing the variable impedance matrices in each jaw together with the series and parallel circuits.

Now turning to FIGS. 11 and 12, another embodiment of jaw structure 200 is illustrated that carries cooperating variable impedance matrices as described above. The upper and lower jaws 212A and 212B have respective engagement surfaces 224A and 224B that carry cooperating variable impedance matrices 125 and 130 as in the previous embodiments of FIGS. 3, 6, 8 and 9. The jaw embodiment of FIGS. 11 and 12 differs in that it is adapted for "one-step" welding and transection of the engaged tissue.

As shown in the embodiments of FIGS. 11 and 12, jaw structure 200 can have an opening-closing mechanism that is capable of applying very high compressive forces on tissue on the basis of cam mechanisms with a reciprocating "I"-beam member 240, wherein jaw closing occurs contemporaneous with Rf energy delivery. Further, the slidable "I"-beam member 240 and the exterior jaw surfaces provide cam surfaces (i) for moving the jaw assembly to the (second) closed position to apply very high compressive forces, and (ii) for moving the jaws toward the (first) open position to apply substantially high opening forces for dissecting tissue. This feature allows the surgeon to insert the tip of the closed jaws into a dissectable tissue plane—and thereafter open the jaws to apply such dissecting forces against tissues. In various embodiments, all or a portion of member 240 can be configured to have "I" shaped cross section. Many prior art instruments are spring-loaded toward the open position and may not be useful for dissecting tissue.

In the embodiment illustrated in FIGS. 11 and 12, the reciprocating "I"-beam member 240 is actuatable from the handle (not shown) of the instrument by any suitable mechanism, such as a lever arm, that is coupled to a proximal end of member 240. The distal end portion 242 of reciprocating "I"-beam member 240 carries first (lower) and second (upper) continuous laterally-extending flange elements 244A and 244B that are coupled by an intermediate transverse element 245. The flange elements 244A and 244B slide in a recessed slot portion 246 in each of the upper and lower jaws (see FIG. 12) to close the jaws and wherein the sliding contact of the lateral edges of flanges 244A and 244B and the side of the recessed slot 246 function to prevent lateral flexing of the jaws. The transverse element 245 and blade edge 250 slide within channels 252 (collectively) in the paired first and second jaws 212A and 212B to thereby open and close the jaws. The transverse element 245 is adapted to transect tissue captured between the jaws with a sharp leading blade edge 250 (FIG. 11). "I"-beam 240 can also be adapted to provide electrosurgical functionality as it transects tissue and has a polarity that matches that of the jaw bodies 232A and 232B which is slidably contacts. The jaw structure of 200 of FIGS. 11 and 12 is described in more complete detail in co-pending U.S. patent application Ser. No. 10/079,728 filed Feb. 19, 2002 titled Electrosurgical Systems and Techniques for Sealing Tissue, and U.S. patent application Ser. No. 10/340,144 filed Jan. 10, 2003 titled Jaw Structure for Electrosurgical Instrument and Method of Use, which are fully incorporated herein by this reference.

Still referring to FIGS. 11 and 12, the first and second jaws 212A and 212B close about an engagement plane 255 wherein the tissue-engaging surface layers 224A and 224B that contact and deliver energy to engaged tissue T as described above. The jaws can have any suitable length with teeth or serrations 256 for gripping various tissues (FIG. 11). One preferred embodiment shown in FIG. 11 provides such teeth 156 at an inner portion of the jaws along channels 248 thus allowing for substantially smooth engagement surface layers 224A and 224B laterally outward of the tissue-gripping elements. The axial length of jaws 212A and 212B can be any suitable length depending on the anatomic structure targeted for transection and sealing and typically will range from about 10 mm. to 50 mm. The jaw assembly can also be configured to apply very high compressive forces over much longer lengths, for example up to about 200 mm., for resecting and sealing organs such as a lung or liver. The scope of the invention also covers jaw assemblies for an instrument used in micro-surgeries (e.g. micro-vascular surgery) wherein the jaw length can be about 5.0 mm or less.

Figure 13:
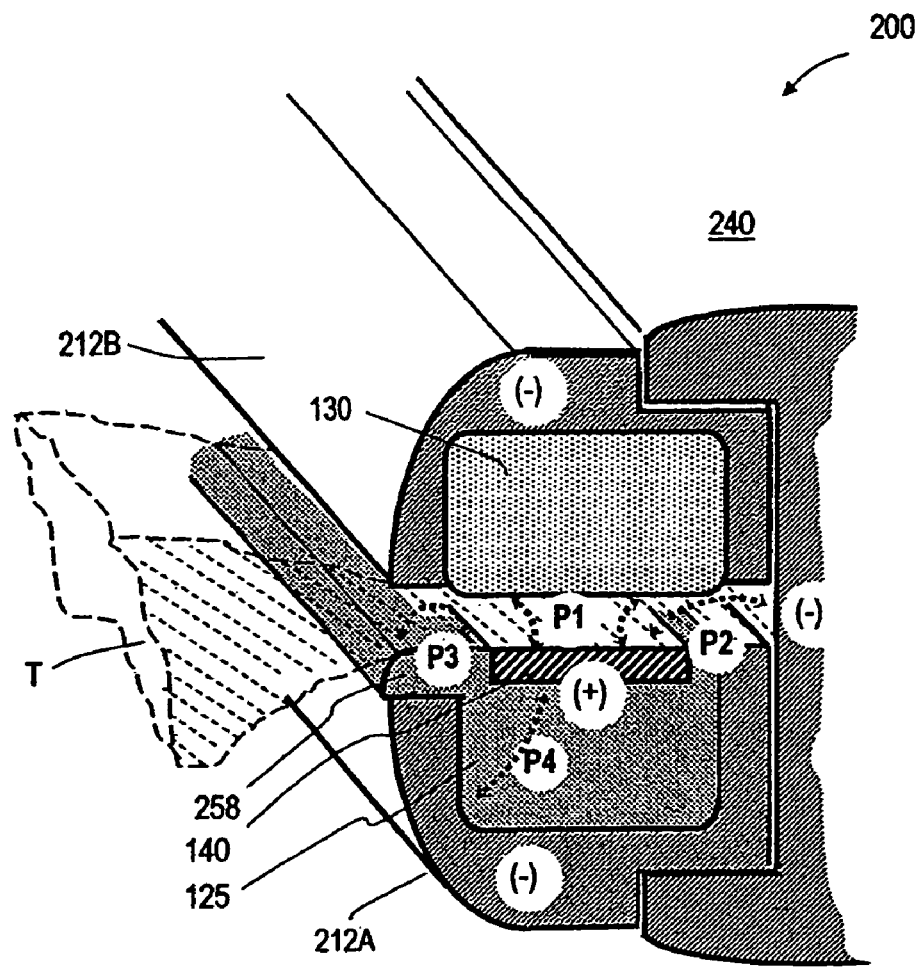
FIG. 13 is an enlarged sectional view of a portion the jaw structure of FIGS. 11-12 showing the potential current paths in engaged tissue and the variable impedance 3D matrix bodies during operation.

In FIGS. 11 and 12, it can be seen that the lower jaw 212A has a variable impedance matrix 125 that has an edge portion 258 that (optionally) extends laterally over the outer edge of the jaw body 232A. This matrix feature has been found useful in modulating Rf energy density in the margin of the treated tissue to create distinct region between welded tissue and unaffected tissue. Also, the upper jaw's matrix 130 can be positioned to extend slightly outward (dimension 262) from the upper jaw body 232B. FIG. 13 illustrates that the jaw structure 200 of FIGS. 11 and 12 provides the multiplicity of flow paths P1-P4 as described previously in FIGS. 10A-10D. In all other electrosurgical aspects, the jaw structure 200 and variable impedance matrices of FIGS. 11 and 12 function as described above with reference to FIGS. 3, 6, 8, 9 and 10A-10D.

Figure 14A:
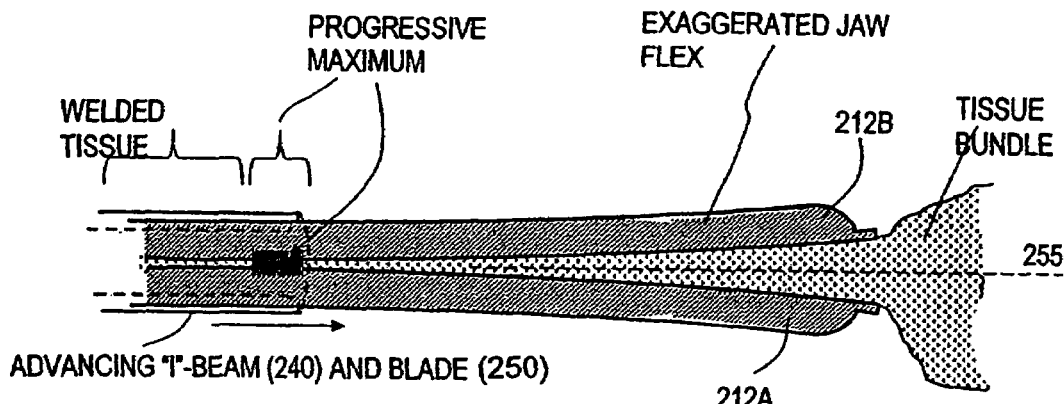
FIGS. 14A-14C are schematic sectional views of the jaw structure of FIGS. 11-13 with elongate jaws progressively engaging, welding and transecting a tissue bundle.
Figure 14B:
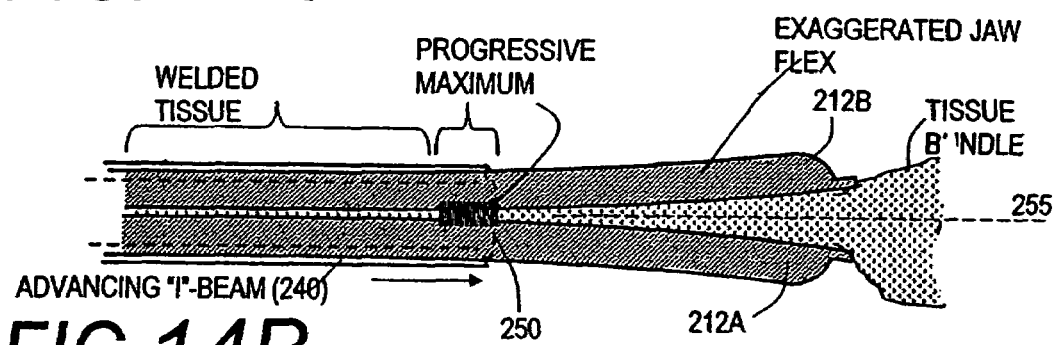
Figure 14C:
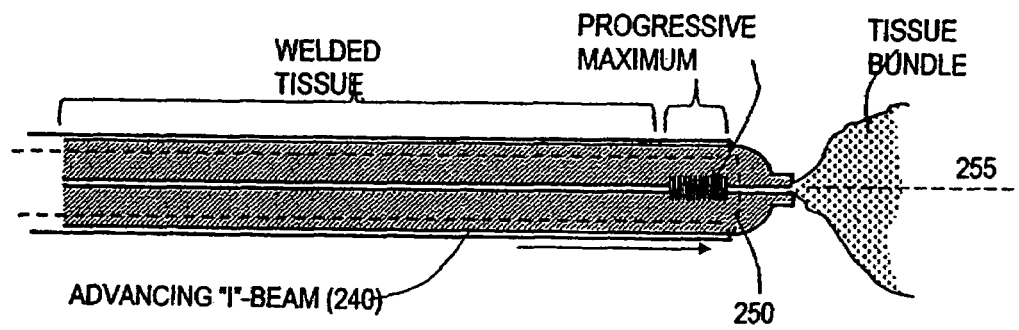

Of particular interest, FIGS. 14A-14C graphically illustrate an embodiment of a one-step sealing and transection method. When using elongated jaws in a small diameter instrument, the issue of jaw flexure when clamping thick tissue bundles typically creates difficulties for both sealing and transection. The jaw structure 200 of FIGS. 11 and 12 solve such problems by applying Rf energy contemporaneously or substantially contemporaneously with jaw closure. Initial Rf energy delivery will begin to dehydrate the engaged tissue T thus, making it possible to compress the tissue to a thin membrane. At the same time, the matrices 125 and 130 will modulate Rf ohmic heating axially along the length of the jaws to thereby insure that thin treated tissue regions in the proximal jaw are not being ohmically heated while more distal regions of the engaged tissue are receiving maximal ohmic heating. All the while, each tissue region containing a different tissue type will receive the optimal Rf energy density based on impedance matching with the adjacent region of a variable impedance matrix.

In FIGS. 14A-14C, the jaws 212A and 212B are shown with a greatly exaggerated flex characteristics to illustrate, in effect, a method of the invention. "I"-beam 240 can be used to compress the tissue T dramatically as it is progressively welded. Thus, a very small jaw structure 200 in a 5 mm. diameter device can chomp down on, weld and transect very thick tissue bundles that are initially up to ½ inch or even 1 inch thick. The highest ohmic heating progresses in a "front" across the tissue and is automatically modulated by the variable impedance matrices 125 and 130 and series-parallel circuitry as described above. Various embodiments of jaw structure 200 further allow the surgeon tactile feedback of the tissue welding process as the advancement of the "I"-beam" 240 indicates that the tissue is welded. This inventive method for welding tissue can be most accurately summarized as the microscale modulation of ohmic active heating in engaged tissue as depicted in FIGS. 10A-10D combined with the progressive macroscale application of ohmic heating as in FIGS. 14A-14C as the blade 245 transects the engaged tissue. The one-step welding and transecting functionality is provided by the use of the high compression "I"-beam for jaw closure and tissue transection together with the cooperating variable impedance component 125 and 130 of the jaw structure.

Figure 15:
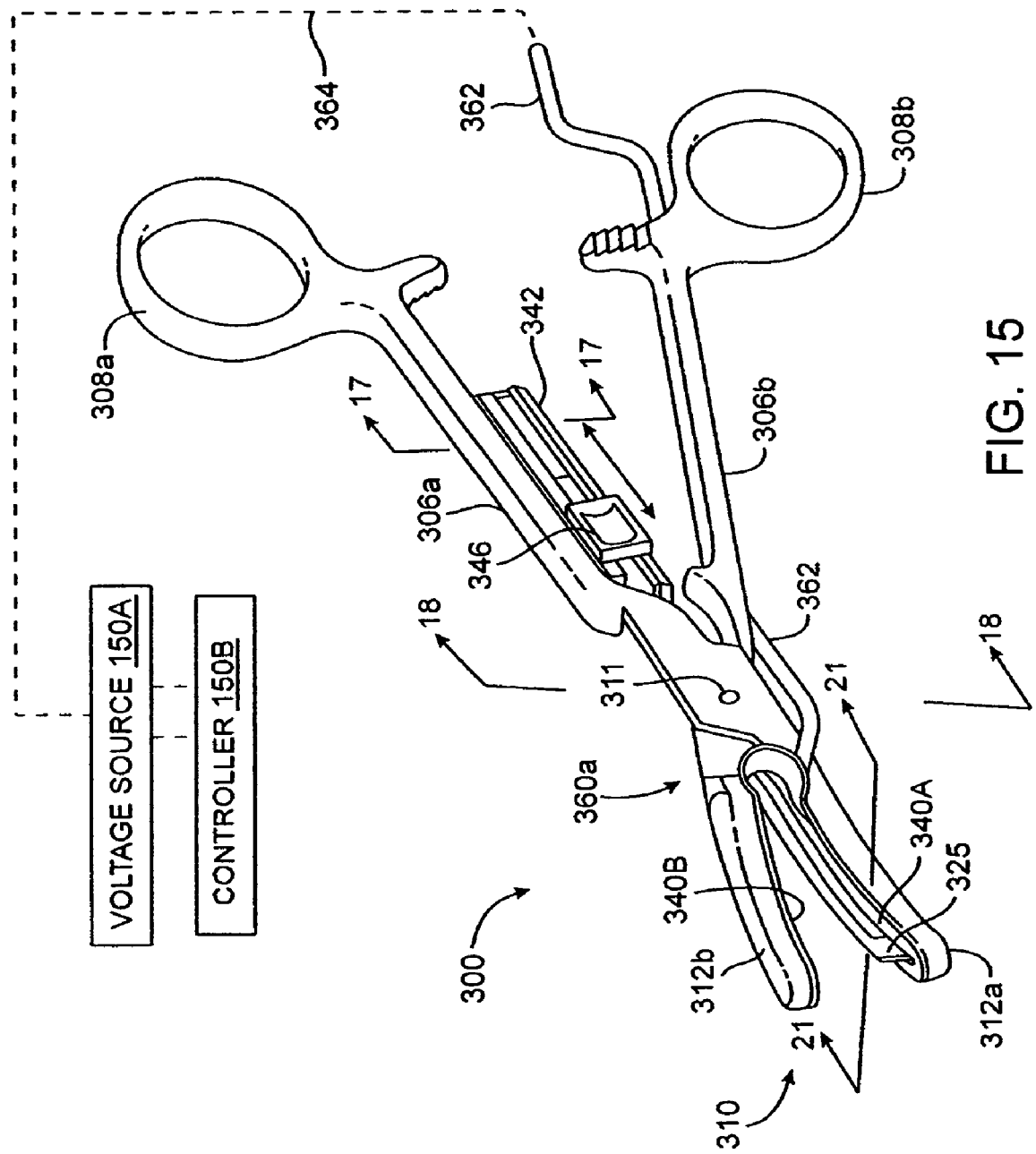
FIG. 15 is a perspective view of a forceps-type instrument with a replaceable electrosurgical-blade cartridge.
Figure 16:
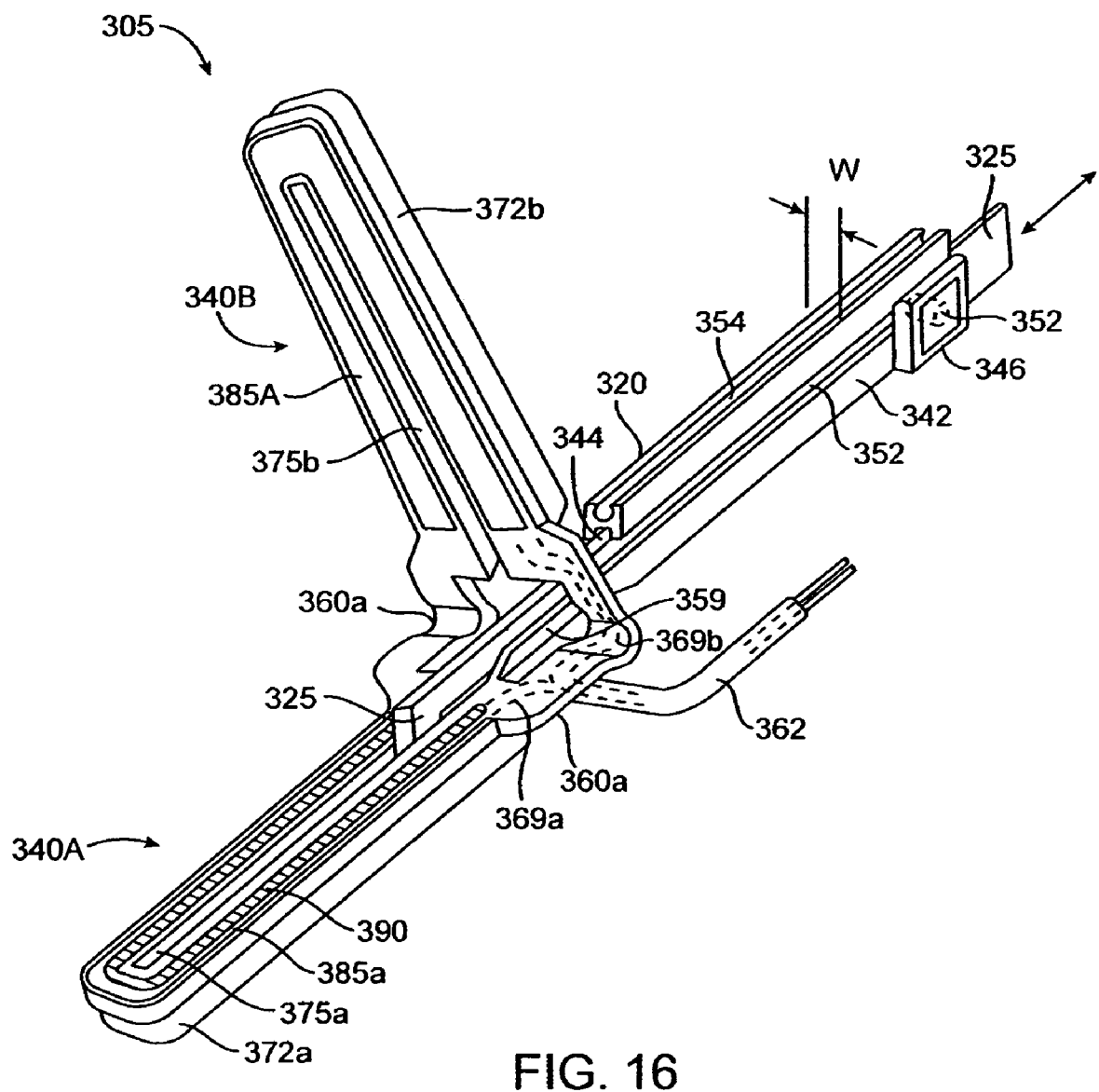
FIG. 16 is a perspective view of the replaceable cartridge de-mated from the forceps of FIG. 15.

3. Disposable cartridge assembly for tissue welding-ligation forceps. FIGS. 15 and 16 illustrate an embodiment of a forceps-type instrument 300 with a single replaceable cartridge 305 (FIG. 16) that carries both electrosurgical and tissue-transection functionality. In one preferred embodiment of FIG. 15, the forceps 300 has first and second handle arm portions 306a and 306b that extend proximally to finger rings 308a and 308b. The instrument has a working end 310 that comprises opposing first and second jaw portions 312a and 312b that are pivotably coupled to allow opening and closing of the jaws. In the embodiment of FIG. 15, the jaws have a simple scissors-type pivot 311, but it should be appreciated, that any multi-link pivot system can be used for additional leverage.

Figure 17:
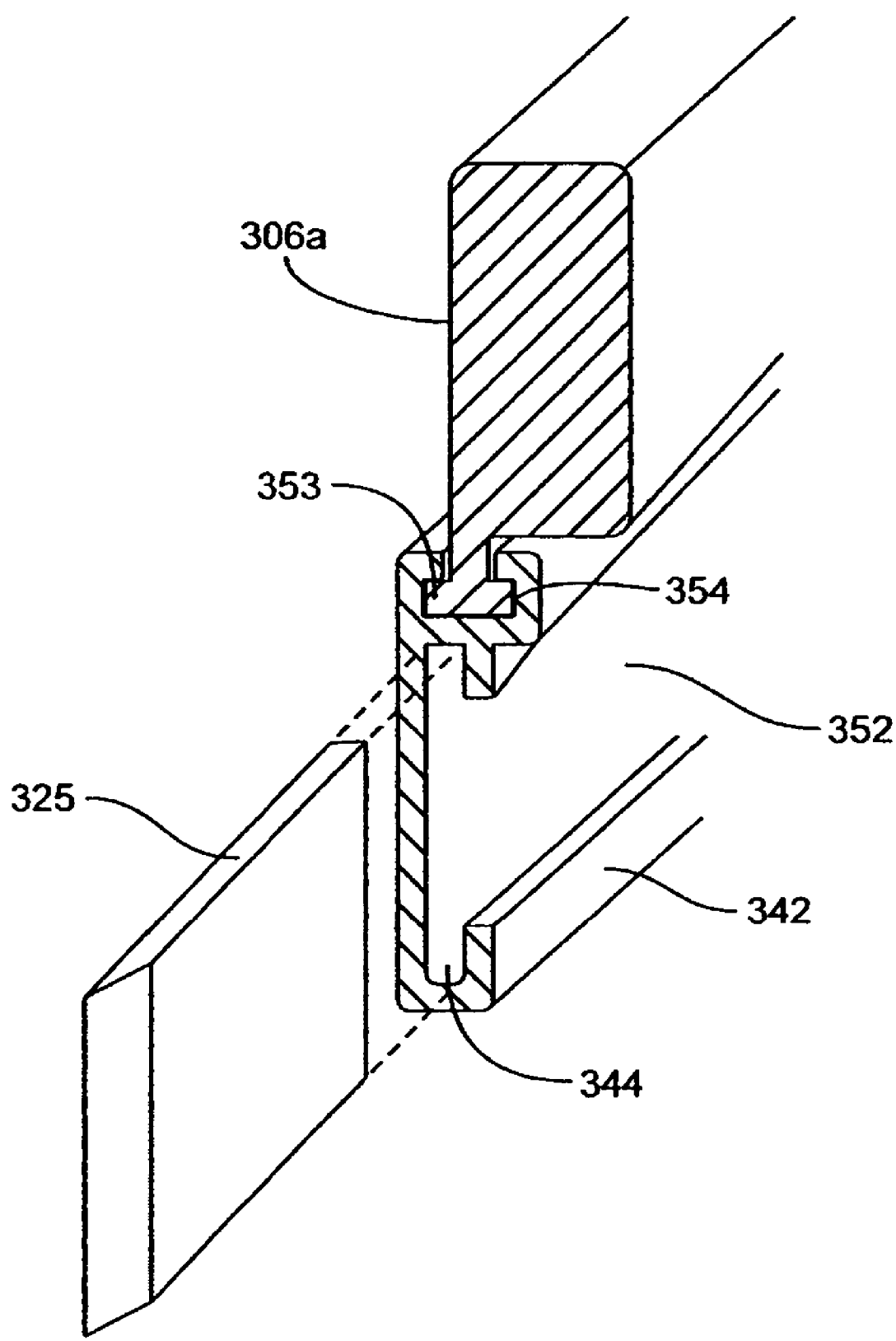
FIG. 17 is a perspective view of a mating portion of the replaceable cartridge of FIG. 16.
Figure 18:
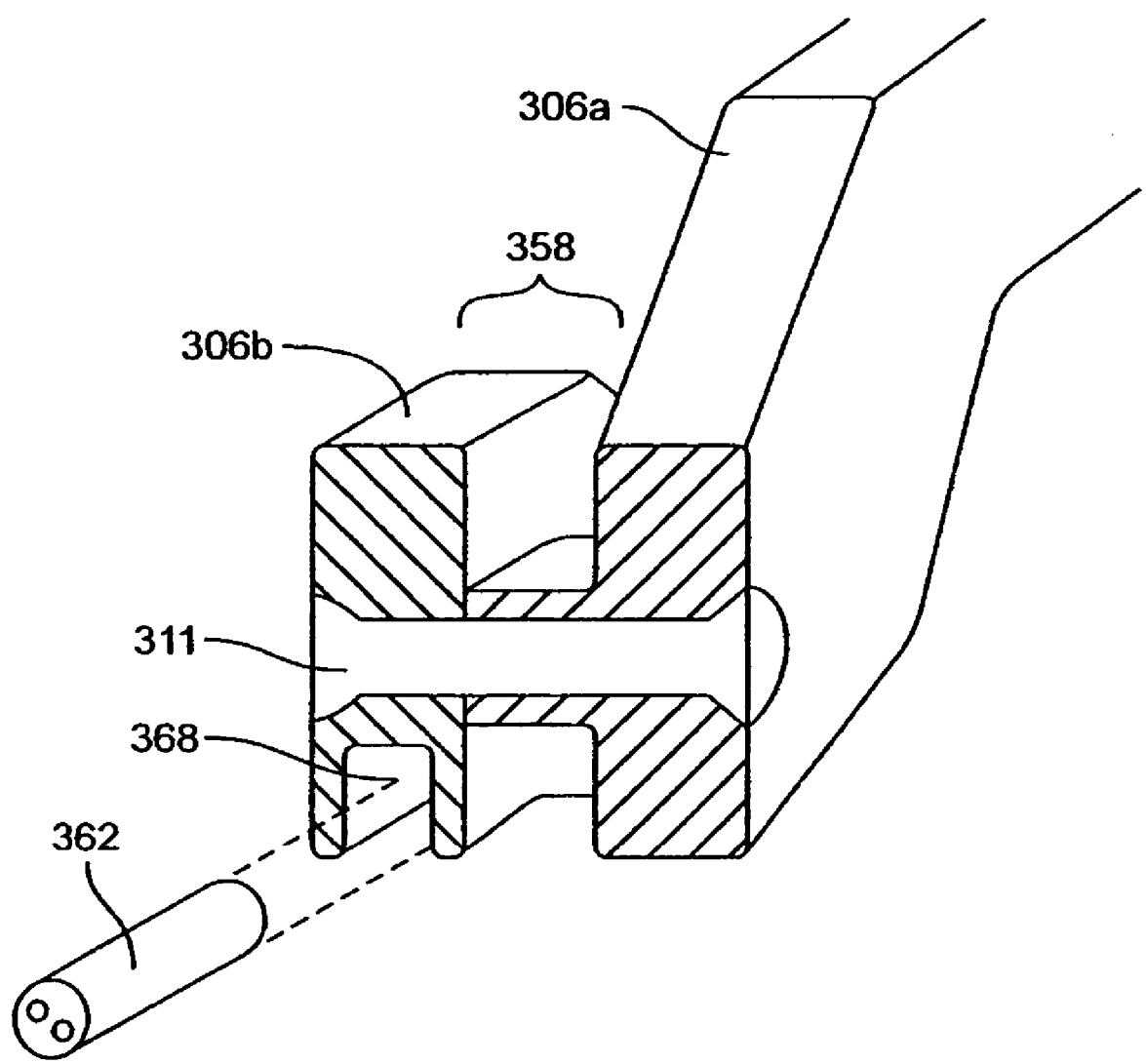
FIG. 18 is a schematic illustration of a cross-sectional view of the forceps.
Figure 19:
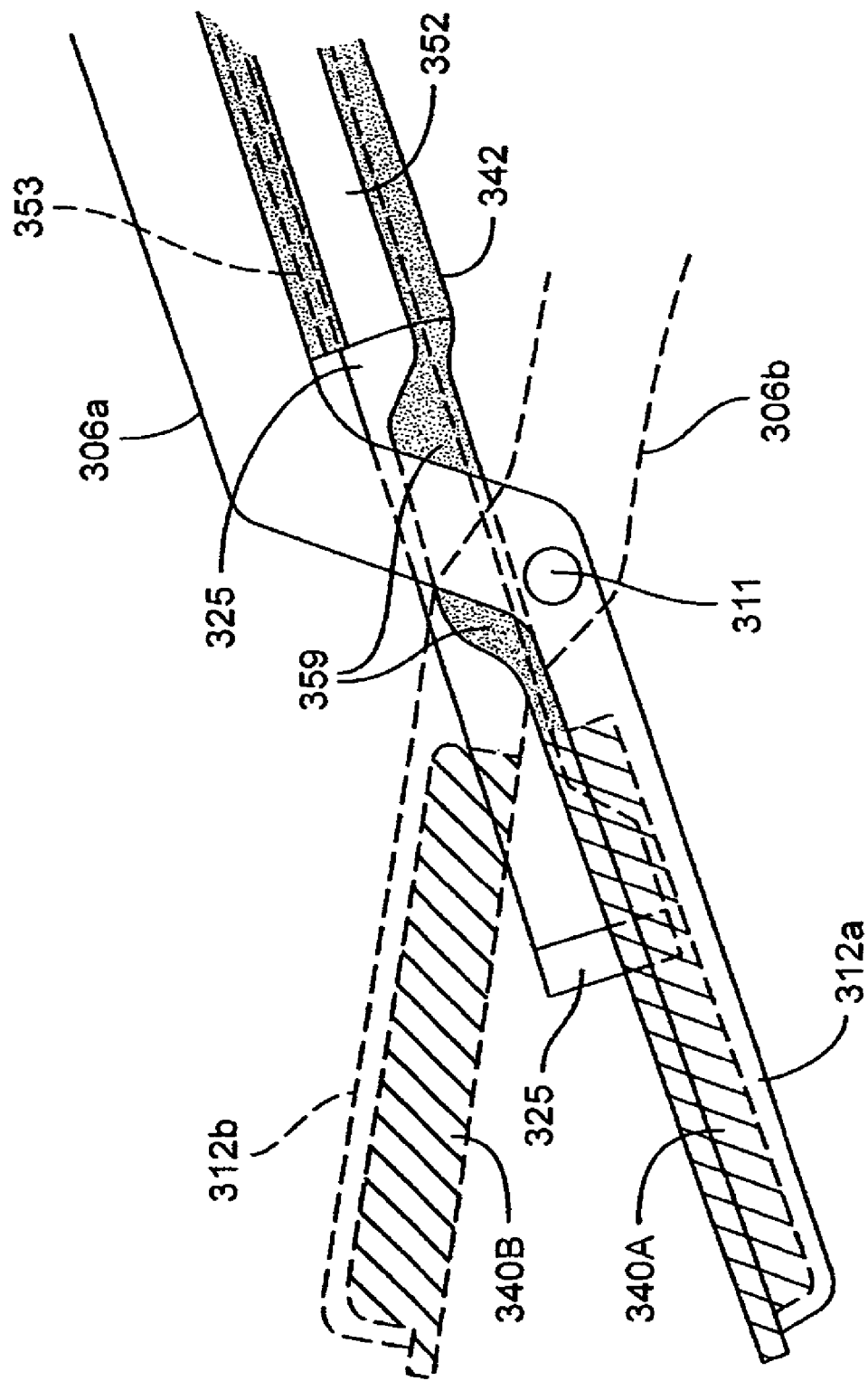
FIG. 19 is a schematic illustration of how the blade can be notched.

Now turning to FIG. 16, in various embodiments, cartridge 305 is adapted for removable engagement with the body of forceps 300. The cartridge 305 comprised a polymer body or housing 320 that carries a slidable blade member 325 as well as first and second energy-delivery elements 340A and 340B flexibly coupled with one another and body 320. The body 320 has a proximal blade housing portion 342 that is configured with a channel 344 that at least partly houses blade member 325. A thumb-grip or other suitable grip 346 is attached to a proximal portion of the blade 325 to actuate the blade between first and second (non-extended and extended) positions to transect tissue when the jaws are in the closed position. Referring to FIG. 16, the thumb-grip 346 is affixed to the blade by a pin 348 that slides in slot 352 of the blade housing portion 342. The blade housing portion 342 is adapted for slidable and removable engagement with a carrier 353 in the arm 306a as best seen in FIGS. 17-19. FIG. 17 illustrates a channel 354 in the polymer body 320 that slides over and engage carrier element 353 of arm 306a. FIG. 18 illustrates a cross-sectional view of the forceps showing a space 358 between the arms 306a and 306b for accommodating the width dimension W of the polymer body 320 (FIG. 16). As can be seen in FIGS. 16 and 19, the body 320 has flexible polymer elements 359 that extend between blade housing portion 342 and the second (lower) energy-delivery elements 340A to provide a unitary disposable cartridge carrying both electrosurgical and blade components. FIG. 19 shows schematically how the blade 325 can be notched and the flexible blade housing 342 can be axially inserted through the space 358 between the jaw arms (FIG. 18) to detachable couple with arm 306a (FIG. 17) before the energy-delivery elements 340A and 340B are inserted into the jaw portions 312a and 312b.

Figure 20:
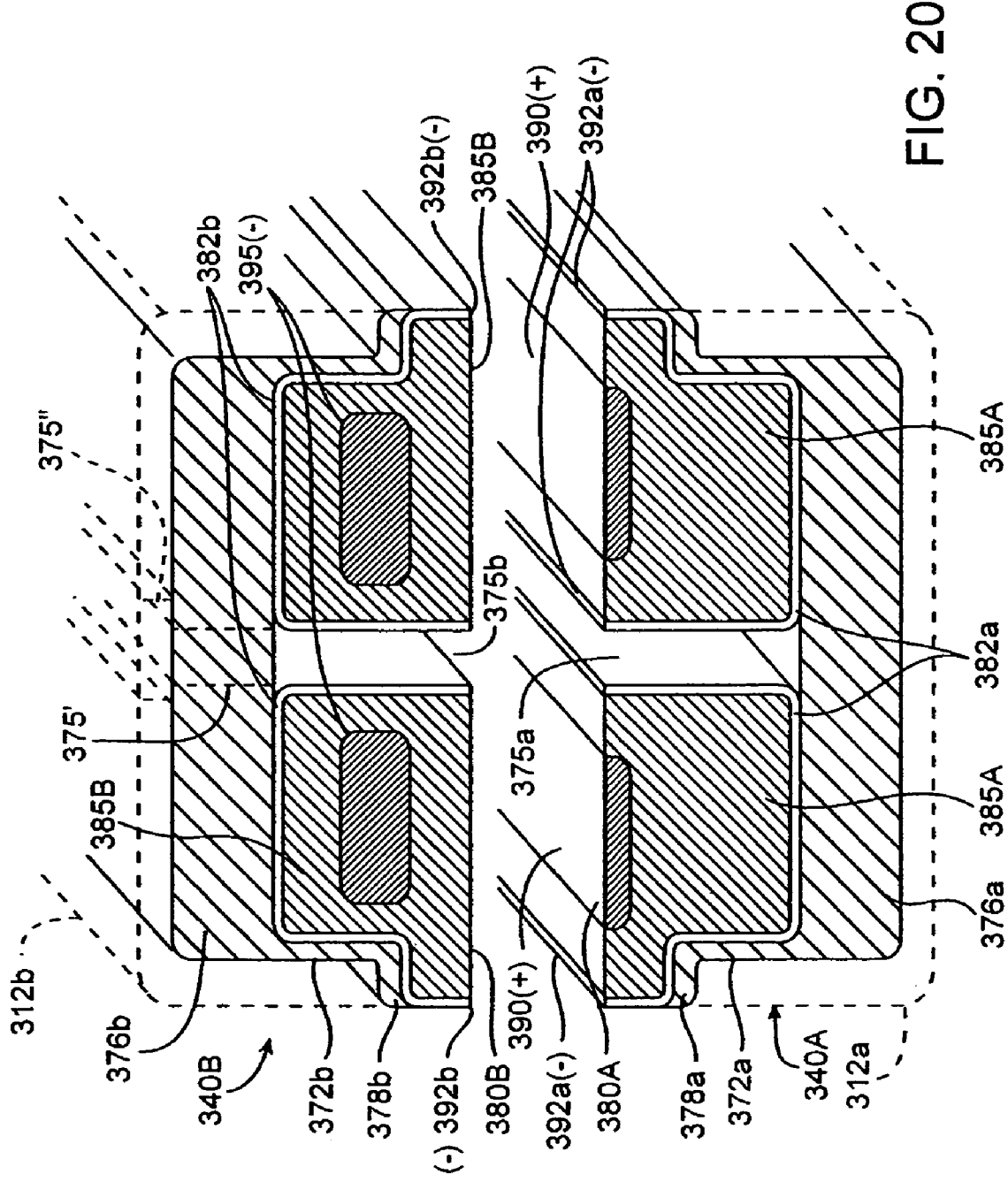
FIG. 20 is a sectional view of the electrosurgical components of the replaceable cartridge of FIG. 15.

Referring back to FIG. 16, the first and second energy-delivery elements 340A and 340B are coupled by flexible hinge elements 360a and 360b, for example, of any suitable resilient polymer. The first and second energy-delivery elements 340A and 340B further are configured for removable engagement with the first and second jaw portions 312a and 312b. As can be seen in FIG. 16, the body 320 also has a flexible electrical lead extending element 362 extending proximally that carries electrical leads for coupling to a cable 364 from a voltage source 150A (FIG. 15). In this embodiment, the flexible extending element 362 is adapted for a slight press fit into a channel 368 in arm 306b of the instrument (see FIGS. 15 and 18), but any means may be suitable for securing the element 362 to the forceps arm to conveniently store the electrical leads so as to not interfere with opening and closing the arms 306a and 306b. The opposing polarity (+) and (−) electrical leads 369a (collectively) within element 362 extend directly to the first (lower) energy-delivery element 340A to couple with the electrical conductors therein (see FIG. 20). At least one electrical lead indicated at 369b extends through flexible hinge element 360b to the second energy-delivery element 340B (FIG. 16). FIG. 20 further describes how the lead 369b is coupled to conductor portions of the second (upper) energy-delivery element 340B.

Any type of mating components of the energy-delivery elements 340A and 340B and jaw portions 312a and 312b fall within the scope of the invention, and FIGS. 16 and 20 indicate that an exemplary lower jaw portion 312a has a "U"-shaped cross-section that receives the body 372a of energy-delivery element 340A. The bodies 372a and 372b of each energy-delivery element 340A and 340B can be dimensioned for a drop-in secure fit in the respective shoe-shaped lower and upper jaw portions. Alternatively, the mating components can have cooperating male and female edges or resilient projecting elements (not shown) as are known in the art to provide detachable secure engagement means between the bodies 372a and 372b of the energy-delivery elements and the jaws.

In one preferred embodiment (FIG. 20) the energy-delivery elements 340A and 340B are both configured with slots or channels indicated at 375a and 375b for receiving the extendable blade member 325. The embodiment of FIG. 20 illustrates partial depth channels for the slidable blade, but the channels can extend through the bodies 372a and 372b as indicated in phantom view of channel 375' in the upper jaw assembly of FIG. 20. Likewise, the jaw portions 312a and 312b also have optional cooperating slots indicated at 375" (phantom view in FIG. 20) adapted for ease of cleaning of the re-usable forceps body 300.

The cross-sectional view of FIG. 20 more particularly illustrates the components and one manner of making the energy-delivery elements 340A and 340B of the assembly, with the upper and lower jaws 312a and 312b in phantom view. The electrosurgical components of each energy-delivery elements (340A and 340B) are similar to that of FIGS. 8 and 12 above, and the method of operation for modulating Rf energy delivery for causing ohmic heating of tissue need not be repeated. Each energy-delivery element (340A and 340B) has a base portion (376a, 376b) and lip portion (378a, 378b) of any non-conductive polymer that contacts the respective jaw body. The planar tissue-engaging surfaces of the energy-delivery elements are indicated at 380A and 380B. Each energy-delivery element (340A and 340B) has a conductive metal shell-like housing portion (382a, 382b) that can be fabricated by stamping, MIM processes or another machining method known in the art. The conductive housing portions (382a, 382b) carry a molded temperature-responsive PTC composition (385A, 385B). The lower engagement surface 380A has a central "U"-shaped electrical conductor portion 390 that extends around blade channel 375a (FIGS. 16 and 20). The electrical conductor portion 390 of the lower engagement surface 380A defines a first polarity in its connection to voltage source 150A. The conductive housing portion 382a defines an opposing second polarity and has edge portions 392a exposed in surface 380A at the laterally outermost edges and along the blade channel 375a. Thus, the opposing polarity conductor portions indicated at (+) and (−) and the variable resistive body portions (385A, 385B) are similar to the embodiment illustrated in FIG. 8. The upper energy-delivery element 340B has an electrode 395 in an interior of the temperature-responsive PTC composition 385B that has an opposing polarity relative to electrode 390 in the opposing energy-delivery element 340A. Further, the upper energy-delivery element 340B has conductive housing portion 382a with edge portions 392b (collectively) in engagement surface 380B that have the same polarity as the conductive housing portion 382a in the opposing energy-delivery element 340A.

In operation, the instrument of FIGS. 15-20 would function exactly as the previously described embodiment of FIGS. 7-10D to cause ohmic heating in tissue. The instrument of FIGS. 17-20 can be used first to grasp and weld tissue, followed by a second step of transecting the engaged tissue. The jaws of the instrument can be straight or curved and the blade 325 can be thin and flexible to allow it to bend as it is advanced through the blade channel portions of the energy-delivery elements. It should be appreciated that the scope of the invention encompasses the flexibly coupled energy-delivery elements 340A and 340B for detachable engagement by opposing jaws when the thermal energy delivery mechanism is of any type known in the art, for example, any resistive heating element for conductive tissue heating or any bi-polar or mono-polar electrode arrangement for causing ohmic tissue heating or a combination thereof.

Figure 21:
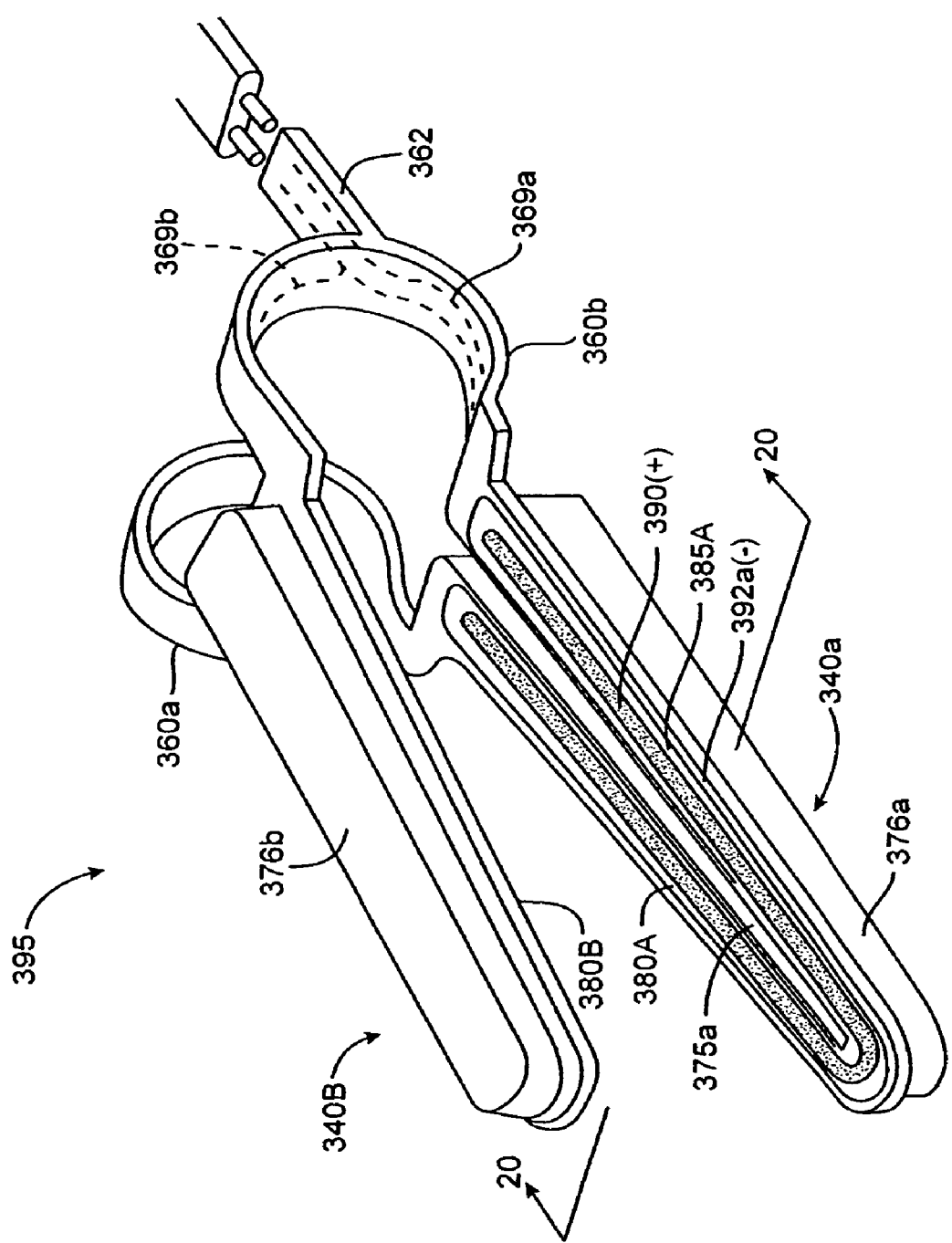
FIG. 21 is a perspective view of an alternative replaceable electrosurgical cartridge without a blade member, the cartridge de-mated from a forceps device.

FIG. 21 illustrates an alternative embodiment of cartridge 395 that carries only electrosurgical components as described above, but without the blade means being integrated into the disposable cartridge. All other components and features are the same as in the cartridge of FIGS. 16 and 20 with like reference numerals describing the components. It should be appreciated that the scope of the invention encompasses the flexibly coupled energy-delivery elements 340A and 340B for detachable engagement by opposing jaws when the thermal energy delivery mechanism is of any type known in the art, for example, any resistive heating element for conductive tissue heating or any bi-polar electrode arrangement for causing ohmic tissue heating, or a combination thereof.

Figure 22:
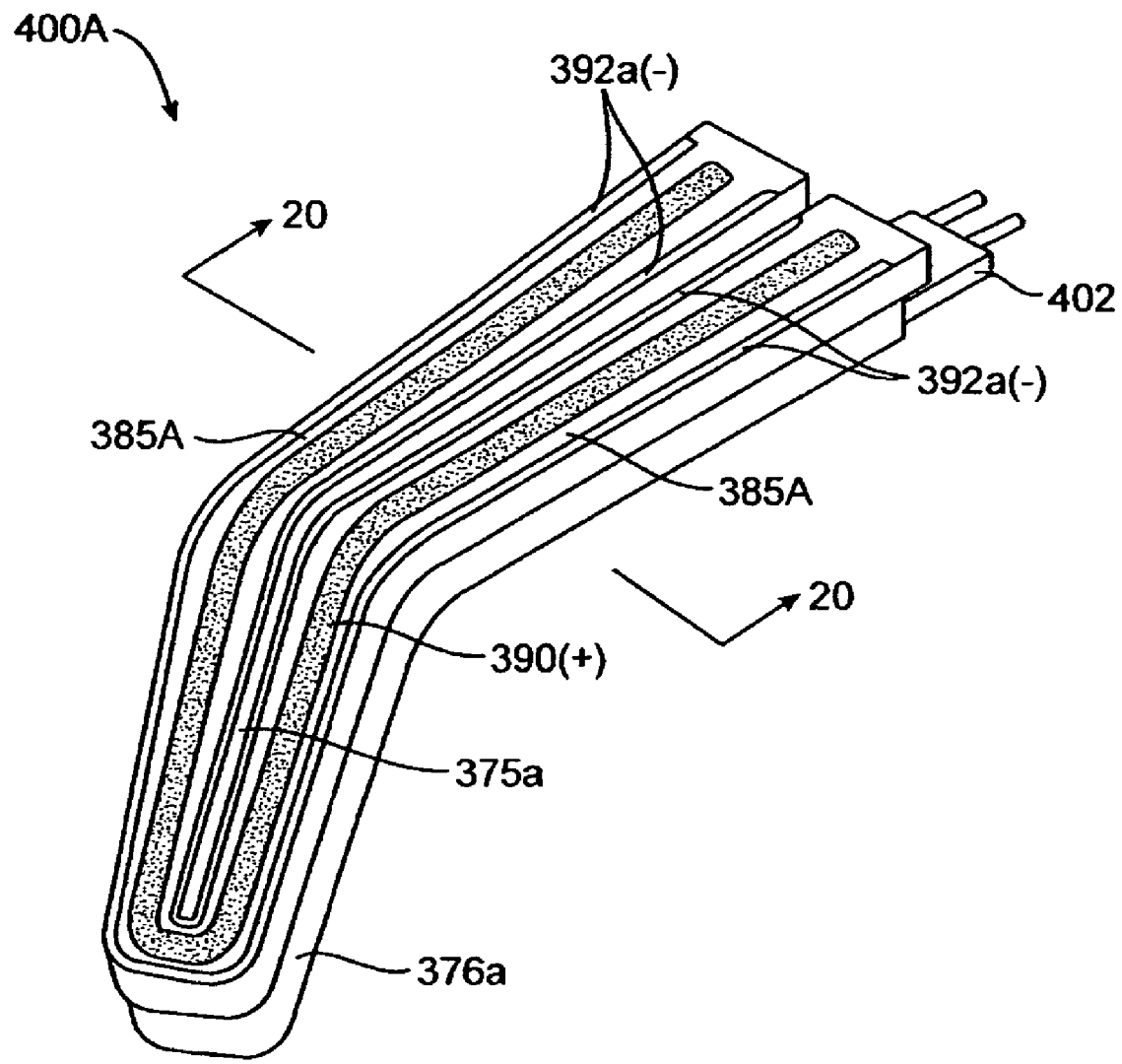
FIG. 22 is a perspective view of an alternative replaceable electrosurgical cartridge for a single jaw member of a forceps device.

FIG. 22 illustrates an alternative embodiment of cartridge or energy-delivery element 400A corresponding to the invention that comprises a single plug-in cartridge for inserting into a single jaw. The embodiment is shown for a curved jaw to cooperate with a flexible blade. The electrode and temperature-responsive PTC component of the element 400A remains the same as in FIG. 20, as indicated by the sectional line. This embodiment has a electrical plug 402 that can inserted into a cooperating connector within the jaw or handle structure, or plug 402 can be any length to couple directly to a cable extending to voltage source 150A. It can be easily understood that a cooperating energy-delivery element (400B not shown) for an opposing jaw can be provided having the components as in FIG. 20.

The foregoing description of various embodiments of the invention has been presented for purposes of illustration and description. It is not intended to limit the invention to the precise forms disclosed. Many modifications, variations and refinements will be apparent to practitioners skilled in the art. Further, the teachings of the invention have broad application in the electrosurgical and laparoscopic device fields as well as other fields which will be recognized by practitioners skilled in the art.

Elements, characteristics, or acts from one embodiment can be readily recombined or substituted with one or more elements, characteristics or acts from other embodiments to form numerous additional embodiments within the scope of the invention Hence, the scope of the present invention is not limited to the specifics of the exemplary embodiment, but is instead limited solely by the appended claims.

What is claimed is:

1. A unitary removable assembly for use with electrosurgical forceps having a pair of opposing jaw portions, the assembly comprising:
   a housing;
   a pair of electrosurgical energy-delivery elements carried by the housing, the energy-delivery elements having opposing tissue-engagement surfaces that are removably engageable with the pair of opposing jaw portions to provide tissue-engagement surfaces in opposing relation to one another; and
   a slidable blade member carried by the housing for slidable actuation relative to the energy delivery elements,
   wherein at least one energy-delivery element of the pair of electrosurgical energy-delivery elements has an engagement surface carrying a temperature-responsive variable resistive body and at least one electrode for causing ohmic heating in engaged tissue, and wherein the engagement surface carries the temperature-responsive variable resistive body adjacent the at least one electrode.

2. A removable assembly as in claim 1, wherein at least one energy-delivery element is coupled to the housing with a flexible structure.

3. A removable assembly as in claim 2, wherein the flexible structure comprises a polymer.

4. A removable assembly as in claim 1, further comprising a connector for coupling at least one energy-delivery element to a voltage source.

5. A removable assembly as in claim 1, wherein each energy-delivery element has an engagement surface carrying an electrode.

6. A removable assembly as in claim 1, wherein each energy-delivery element has an engagement surface carrying a temperature-responsive variable resistive body for responding to the temperature of engaged tissue.

7. A removable assembly as in claim 6, wherein the temperature-responsive variable resistive body comprises a composition having a positive temperature coefficient of resistance or a composition having negative temperature coefficient of resistance.

8. A removable assembly as in claim 1, wherein an energy-delivery element has an engagement surface carrying a temperature-responsive variable resistive body and opposing polarity electrodes.

9. A removable assembly as in claim 8, wherein the engagement surface carries the temperature-responsive variable resistive body intermediate the opposing polarity electrodes.

10. A removable assembly as in claim 1, wherein the blade member is flexible.

11. A removable assembly as in claim 1, wherein the blade member has a distally-facing sharp edge.

12. A removable assembly as in claim 1, wherein the blade member has a proximally-facing sharp edge.

13. A removable assembly as in claim 1, wherein at least one energy-delivery element has a channel for slidably receiving the blade member.

14. A unitary removable assembly for use with electrosurgical forceps having a pair of opposing jaw portions, the assembly comprising:
   a housing means;
   a pair of electrosurgical energy-delivery elements carried by the housing means, the energy-delivery elements having opposing tissue-engagement surfaces that are removably engageable with the pair of opposing jaw portions to provide tissue-engagement surfaces in opposing relation to one another; and
   a slidable cutting means carried by the housing means,
   wherein at least one electrosurgical energy-delivery element of the pair of electrosurgical energy-delivery elements has an engagement surface carrying a temperature-responsive variable resistive body and opposing polarity electrodes, and wherein the engagement surface carries the temperature-responsive variable resistive body intermediate the opposing polarity electrodes.

* * * * *

UNITED STATES PATENT AND TRADEMARK OFFICE
CERTIFICATE OF CORRECTION

| | | |
|---|---|---|
| PATENT NO. | : 7,632,269 B2 | Page 1 of 1 |
| APPLICATION NO. | : 11/038930 | |
| DATED | : December 15, 2009 | |
| INVENTOR(S) | : Truckai et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 661 days.

Delete the phrase "by 661 days" and insert -- by 1233 days --

Signed and Sealed this

Eighth Day of June, 2010

David J. Kappos
*Director of the United States Patent and Trademark Office*